US010524786B2

(12) United States Patent
Khan

(10) Patent No.: US 10,524,786 B2
(45) Date of Patent: Jan. 7, 2020

(54) SPRING-CLOSING ENDOSCOPIC CLIP WHERE THE SPRING ACTION CAN ALSO REVERSE THE CLIP PRIOR ANYTIME BEFORE FULL EJECTION

(71) Applicant: Mubashir H. Khan, Springfiled, MO (US)

(72) Inventor: Mubashir H. Khan, Springfiled, MO (US)

( * ) Notice: Subject to any disclaimer, the term of this patent is extended or adjusted under 35 U.S.C. 154(b) by 368 days.

(21) Appl. No.: 15/283,890

(22) Filed: Oct. 3, 2016

(65) Prior Publication Data

US 2017/0086824 A1  Mar. 30, 2017

Related U.S. Application Data

(63) Continuation-in-part of application No. 14/834,186, filed on Aug. 24, 2015, now abandoned, which is a continuation-in-part of application No. 14/721,321, filed on May 26, 2015, now Pat. No. 9,708,818, said application No. 14/721,321 is a continuation-in-part of application No. 14/276,513, filed on May 13, 2014, now abandoned.

(60) Provisional application No. 62/378,390, filed on Aug. 23, 2016, provisional application No. 62/291,131, filed on Feb. 4, 2016, provisional application No.
(Continued)

(51) Int. Cl.
*A61B 17/068* (2006.01)
*A61B 17/122* (2006.01)
*A61B 17/128* (2006.01)

(52) U.S. Cl.
CPC ........ *A61B 17/068* (2013.01); *A61B 17/1227* (2013.01); *A61B 17/1285* (2013.01); *A61B 2017/0688* (2013.01)

(58) Field of Classification Search
CPC .............. A61B 17/1227; A61B 17/128; A61B 17/1285; A61B 17/122; A61B 17/1222; A61B 17/1225; A61B 17/08; A61B 17/083; A61B 17/085; A61B 17/068; A61B 17/0684; A61B 17/0686; A61B 17/0682; A61B 17/10; A61B 17/105; A61B 17/072; A61B 17/07207; A61B 17/0644; A61B 17/0057; A61B 17/12; A61B 17/12013; A61B 2017/081; A61B 2017/088; A61B 2017/0688; A61B 2017/0645; A61B 2017/0668; A61B 2017/12004; Y10S 227/901; Y10S 227/902
USPC .......................... 606/142, 143, 151, 157, 158
See application file for complete search history.

(56) References Cited

U.S. PATENT DOCUMENTS

| 188,355 A | 3/1877 | Goddu ........................ 411/445 |
| 711,169 A | 10/1902 | LeBlanc ...................... 74/127 |

(Continued)

FOREIGN PATENT DOCUMENTS

GB  1 452 185  5/1974  ............. A61B 17/42

*Primary Examiner* — Katherine H Schwiker
(74) *Attorney, Agent, or Firm* — Jonathan A. Bay

(57) ABSTRACT

Endoscopic surgery clips are dispensed out of an endoscopic catheter that has restriction provisions that cooperate with spring-biased jaw-clenching provision(s) that are provided to the clips. The cooperation between the restrictions of the catheter and spring-biased jaw-clenching provisions of the clips cooperate to facilitate reversal of the lead clip to-be-ejected, prior anytime before full ejection past the dispensing end of the endoscopic catheter, and at least partially reversed back into the lumen therefor in the endoscopic catheter.

8 Claims, 25 Drawing Sheets

Related U.S. Application Data

62/236,461, filed on Oct. 2, 2015, provisional application No. 62/081,755, filed on Nov. 19, 2014, provisional application No. 62/076,149, filed on Nov. 6, 2014, provisional application No. 62/073,664, filed on Oct. 31, 2014, provisional application No. 62/040,908, filed on Aug. 22, 2014, provisional application No. 62/016,717, filed on Jun. 25, 2014, provisional application No. 62/002,691, filed on May 23, 2014, provisional application No. 61/961,842, filed on Oct. 24, 2013, provisional application No. 61/957,306, filed on Jun. 29, 2013, provisional application No. 61/855,313, filed on May 14, 2013.

(56) References Cited

U.S. PATENT DOCUMENTS

| | | | | |
|---|---|---|---|---|
| 861,188 | A | 7/1907 | Jones | 411/446 |
| 1,031,431 | A | 7/1912 | Dunn | 411/448 |
| 1,878,053 | A | 9/1932 | Winger | 192/44 |
| 2,277,931 | A | 3/1942 | Moe | 411/444 |
| 2,487,803 | A | 11/1949 | Heimann | 411/517 |
| 2,597,344 | A | 5/1952 | Lang | 411/449 |
| 2,631,584 | A | 3/1953 | Purificato | 606/68 |
| 3,051,499 | A | 8/1962 | Minegishi | 277/481 |
| 3,086,208 | A | 4/1963 | Eby | 206/339 |
| 3,098,232 | A | 7/1963 | Brown | 606/143 |
| 3,498,175 | A | 3/1970 | Goodstein | 411/548 |
| 3,958,576 | A | 5/1976 | Komiya | 606/142 |
| 4,246,903 | A | 1/1981 | Larkin | 606/143 |
| 4,265,226 | A | 5/1981 | Cassimally | 606/221 |
| 4,512,345 | A | 4/1985 | Green | 606/143 |
| 4,557,263 | A | 12/1985 | Green | 606/143 |
| 4,589,416 | A | 5/1986 | Green | 606/220 |
| 4,719,917 | A | 1/1988 | Barrows et al. | 606/220 |
| 4,796,627 | A | 1/1989 | Tucker | 606/143 |
| 4,905,691 | A | 3/1990 | Rydell | 606/47 |
| 5,049,152 | A | 9/1991 | Simon et al. | 602/143 |
| 5,122,147 | A | 6/1992 | Sewell | 606/110 |
| 5,156,609 | A | 10/1992 | Nakao et al. | 606/142 |
| 5,207,692 | A | 5/1993 | Kraus | 227/901 |
| 5,242,456 | A | 9/1993 | Nash | 606/139 |
| 5,282,808 | A | 2/1994 | Kovac et al. | 606/143 |
| 5,304,183 | A | 4/1994 | Gourlay et al. | 606/142 |
| 5,336,227 | A | 8/1994 | Nakao | 600/106 |
| 5,340,360 | A | 8/1994 | Stefanchik | 606/142 |
| 5,354,304 | A | 10/1994 | Allen | A61B 17/122 |
| 5,366,459 | A | 11/1994 | Yoon | 606/151 |
| 5,433,721 | A | 7/1995 | Hooven et al. | 606/143 |
| 5,462,558 | A | 10/1995 | Kolesa et al. | 606/139 |
| 5,486,182 | A | 1/1996 | Nakao | 600/37 |
| 5,535,759 | A | 7/1996 | Wilk | 128/898 |
| 5,547,474 | A | 8/1996 | Kloeckl et al. | 606/143 |
| 5,626,585 | A | 5/1997 | Mittelstadt et al. | 606/143 |
| 5,746,747 | A | 5/1998 | McKeating | 606/110 |
| 5,772,379 | A | 6/1998 | Evensen | 411/442 |
| 5,814,052 | A | 9/1998 | Nakao | 606/110 |
| 5,846,248 | A | 12/1998 | Chu | 606/113 |
| 5,906,620 | A | 5/1999 | Nakao | 606/113 |
| 6,010,512 | A | 1/2000 | Chu | 606/113 |
| 6,015,415 | A | 1/2000 | Avellanet | 606/110 |
| 6,071,233 | A | 6/2000 | Ishikawa | 600/104 |
| 6,090,129 | A | 7/2000 | Ouchi | 606/113 |
| 6,171,315 | B1 | 1/2001 | Chu | 606/113 |
| 6,352,541 | B1 | 3/2002 | Kienzle | A61B 17/1285 |
| 6,375,661 | B2 | 4/2002 | Chu | 606/113 |
| 6,599,298 | B1 | 7/2003 | Forster et al. | 606/139 |
| 6,616,654 | B2 | 9/2003 | Mollenauer | 606/110 |
| 6,616,659 | B1 | 9/2003 | de la Torre | 128/898 |
| 6,679,892 | B2 | 1/2004 | Guido | 606/113 |
| 6,843,794 | B2 | 1/2005 | Sixto, Jr. et al. | 605/142 |
| 7,001,399 | B2 | 2/2006 | Damarati | 606/143 |
| 7,044,947 | B2 | 5/2006 | de la Torre | 128/898 |
| 7,081,121 | B2 | 7/2006 | Muramatsu et al. | 606/142 |
| 7,094,245 | B2 | 8/2006 | Adams et al. | 606/142 |
| 7,223,271 | B2 | 6/2007 | Muramatsu et al. | 606/143 |
| 7,285,115 | B2 | 10/2007 | Terakura | 606/1 |
| 7,635,374 | B2 | 12/2009 | Monassevitch | 600/104 |
| 7,648,514 | B1 | 1/2010 | Nakao | 606/142 |
| 7,740,639 | B2 | 6/2010 | Hummel | 606/139 |
| 8,070,756 | B2 | 12/2011 | Secrest | 600/564 |
| 8,080,021 | B2 | 12/2011 | Griego | 606/143 |
| 8,123,795 | B1 | 2/2012 | Knodel et al. | 623/1.23 |
| 8,407,875 | B2 | 4/2013 | Gray et al. | 29/268 |
| 8,439,245 | B2 | 5/2013 | Knodel et al. | 227/175.1 |
| 8,631,992 | B1 | 1/2014 | Hausen et al. | 227/179.1 |
| 8,652,146 | B2 | 2/2014 | Hewitt | 606/113 |
| 8,679,155 | B2 | 3/2014 | Knodel et al. | 606/219 |
| 8,979,836 | B2 | 3/2015 | Fischer | 606/41 |
| 9,463,039 | B2 | 10/2016 | Kuroda | |
| 2001/0000348 | A1 | 4/2001 | Chu | 606/113 |
| 2002/0091399 | A1* | 7/2002 | Ben David | A61B 17/0057 606/158 |
| 2002/0133178 | A1* | 9/2002 | Muramatsu | A61B 17/1227 606/142 |
| 2003/0023237 | A1 | 1/2003 | Mollenauer | 606/27 |
| 2003/0065335 | A1 | 4/2003 | Guido | 606/144 |
| 2003/0236535 | A1 | 12/2003 | Onuki | 606/144 |
| 2004/0044335 | A1 | 3/2004 | de la Torre | 606/27 |
| 2004/0225183 | A1 | 11/2004 | Michlitsch | A61B 1/00135 |
| 2005/0107807 | A1 | 5/2005 | Nakao | A61B 17/122 |
| 2005/0107809 | A1 | 5/2005 | Litscher et al. | 606/142 |
| 2005/0209590 | A1 | 9/2005 | Terakura | 606/47 |
| 2005/0216036 | A1 | 9/2005 | Nakao | A61B 17/068 |
| 2006/0235433 | A1 | 10/2006 | Secrest | 606/114 |
| 2006/0253128 | A1 | 11/2006 | Sekine | 606/139 |
| 2006/0271072 | A1 | 11/2006 | Hummel | 606/142 |
| 2007/0213585 | A1 | 9/2007 | Monassevitch | 600/104 |
| 2008/0208217 | A1 | 8/2008 | Adams | 606/143 |
| 2008/0255427 | A1 | 10/2008 | Satake et al. | 600/204 |
| 2009/0069805 | A1 | 3/2009 | Fischer | 606/42 |
| 2009/0105533 | A1* | 4/2009 | Fujita | A61B 17/1227 600/104 |
| 2009/0131749 | A1 | 5/2009 | Ahmed | 600/106 |
| 2010/0044251 | A1* | 2/2010 | Itoh | A61B 17/1227 206/63.3 |
| 2010/0049217 | A1* | 2/2010 | Matsuoka | A61B 17/1227 606/143 |
| 2010/0292715 | A1 | 11/2010 | Nering | A61B 17/064 |
| 2011/0112434 | A1 | 5/2011 | Ghabrial | 600/564 |
| 2011/0184429 | A1 | 7/2011 | Saldinger | 606/113 |
| 2011/0224492 | A1 | 9/2011 | Stern | 600/153 |
| 2011/0313437 | A1 | 12/2011 | Yeh | A61B 17/122 |
| 2012/0029526 | A1 | 2/2012 | Hewitt | 606/113 |
| 2012/0226287 | A1 | 9/2012 | Qadeer | 606/113 |
| 2013/0131688 | A1 | 5/2013 | Schwartz | 606/113 |
| 2013/0211432 | A1* | 8/2013 | Terada | A61B 17/122 606/151 |
| 2013/0331854 | A1 | 12/2013 | Saldinger | 606/113 |
| 2014/0074143 | A1* | 3/2014 | Fitzgerald | A61B 17/10 606/199 |
| 2015/0032119 | A1 | 1/2015 | Kuroda | 606/113 |
| 2015/0272588 | A1 | 10/2015 | Khan | 606/130 |
| 2015/0374392 | A1 | 12/2015 | Khan | 606/113 |
| 2016/0095598 | A1 | 4/2016 | Khan | 606/143 |
| 2016/0354070 | A1 | 12/2016 | Motai | |

* cited by examiner

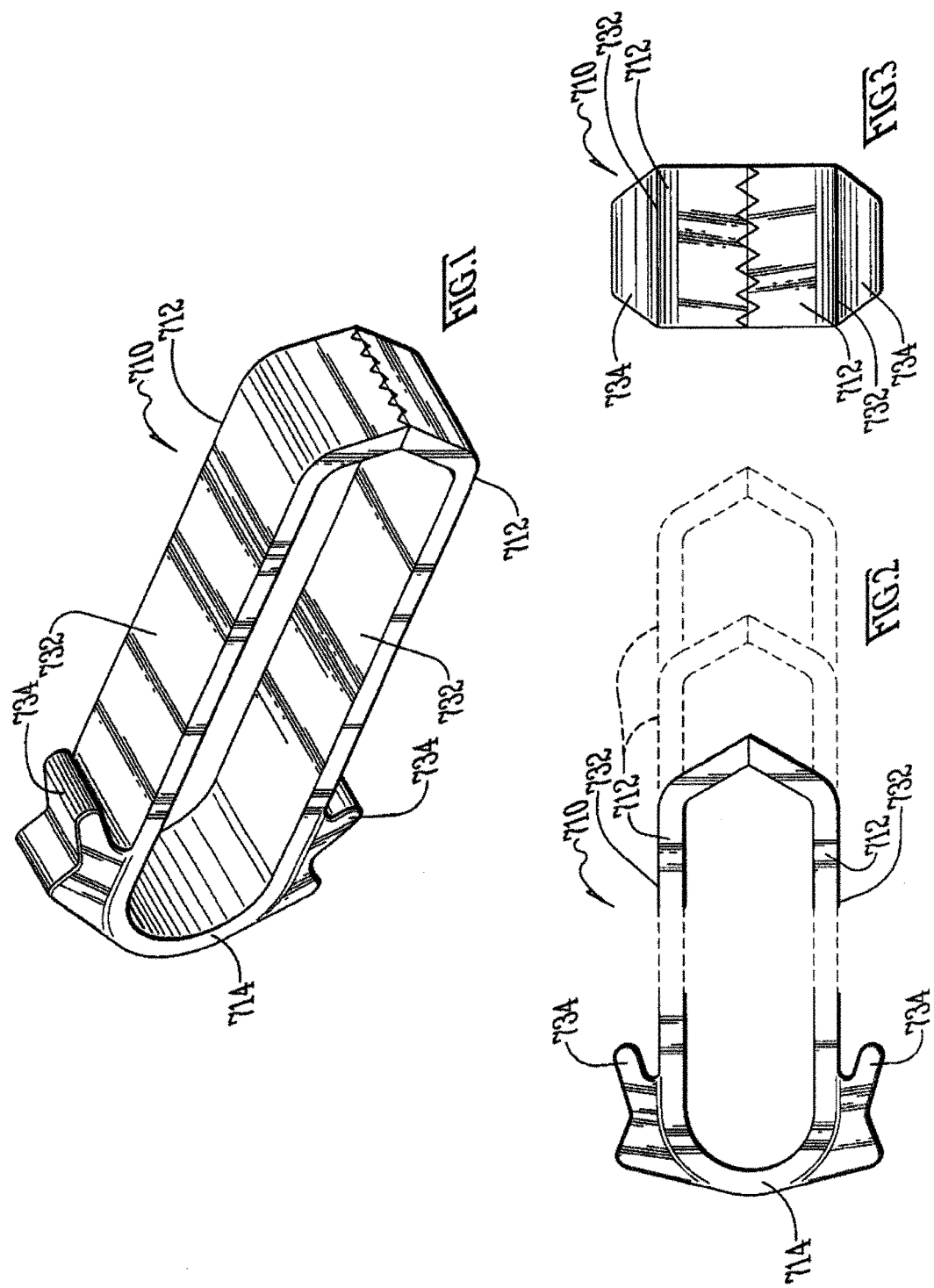

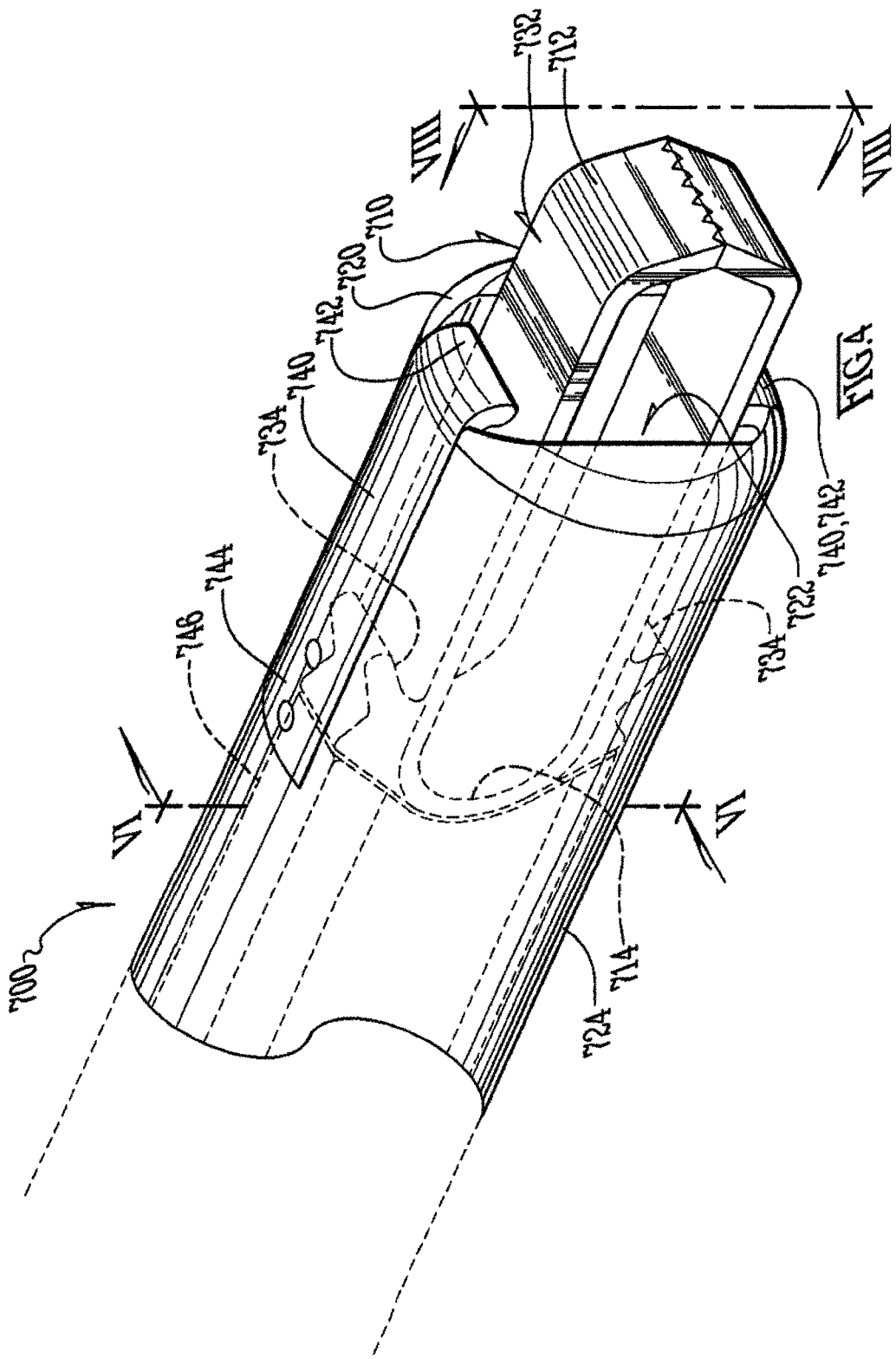

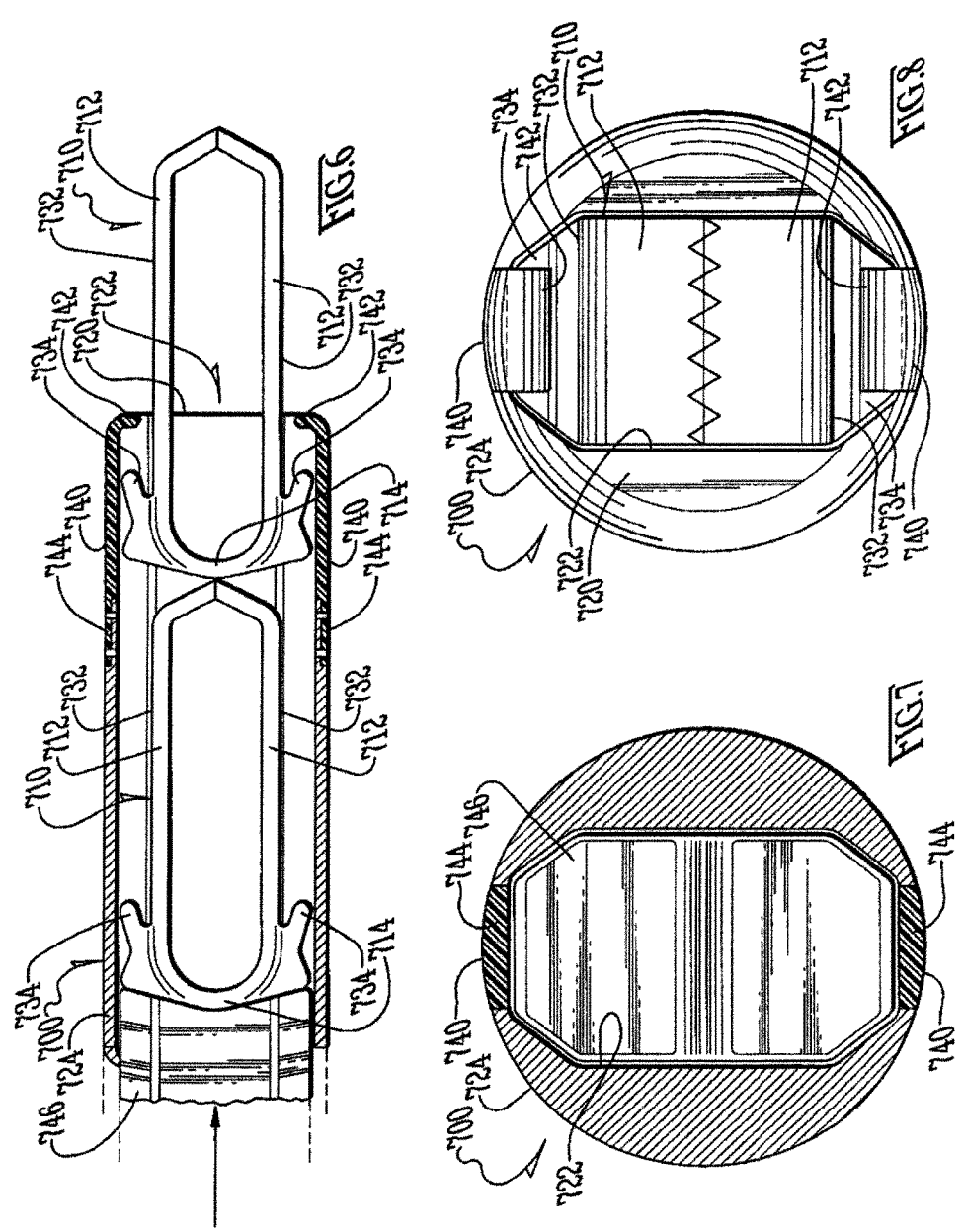

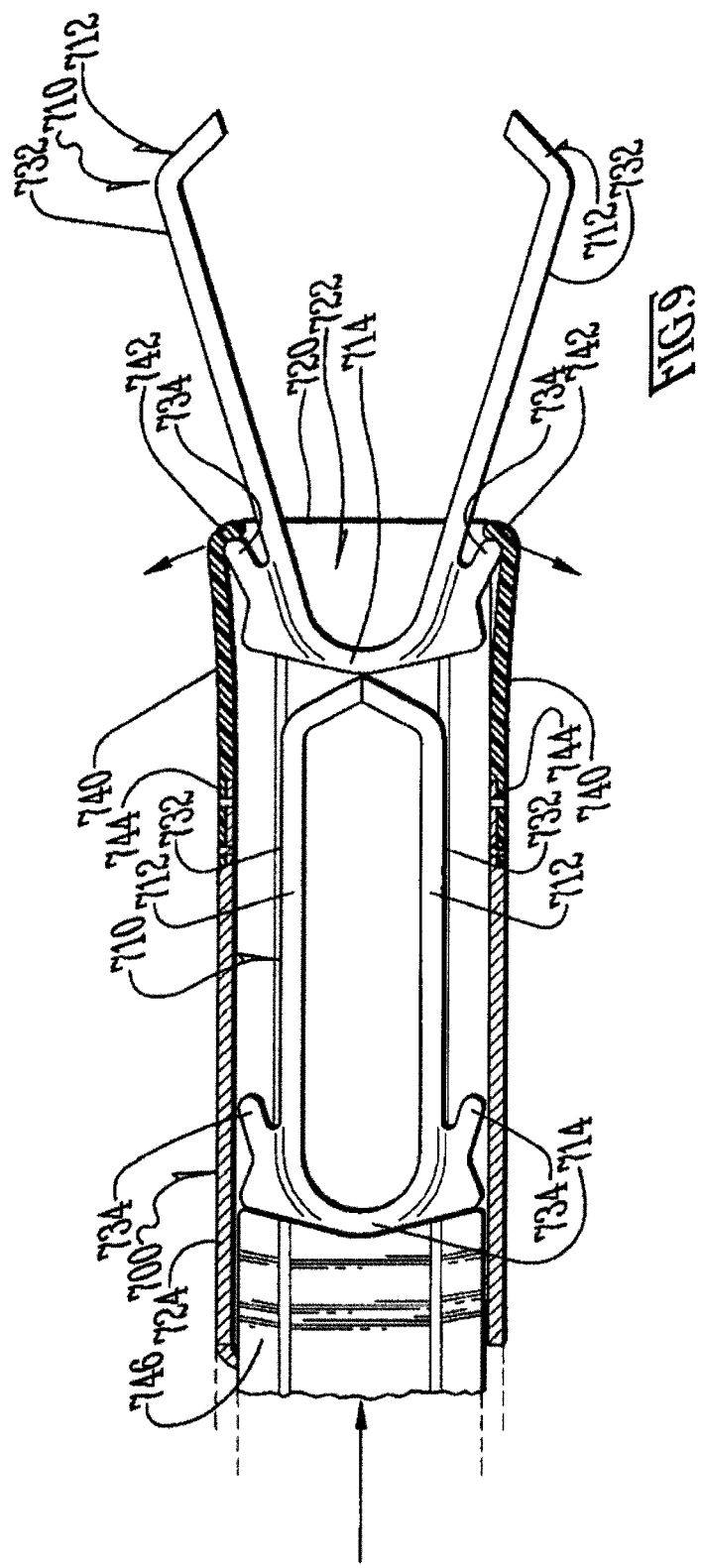

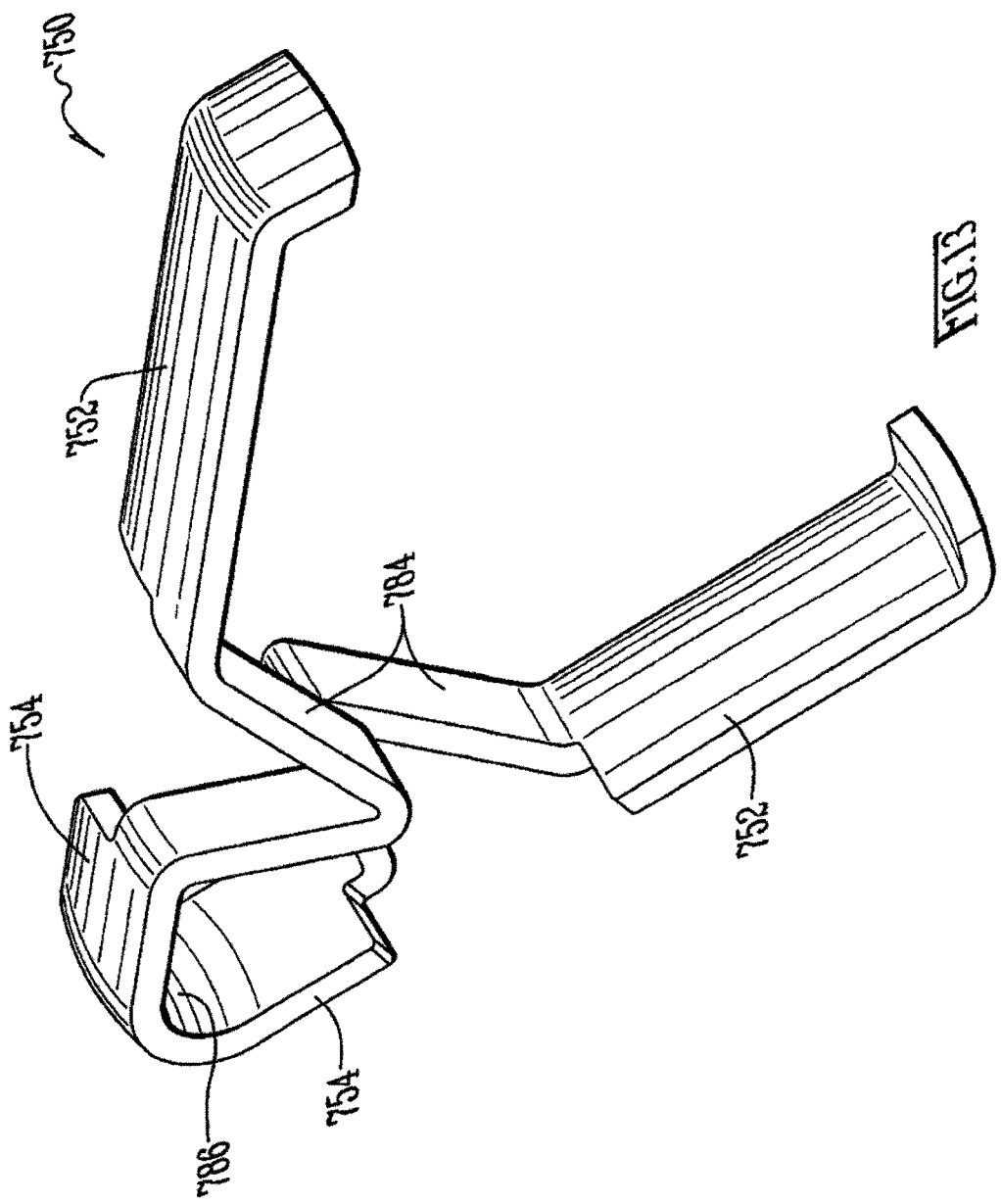

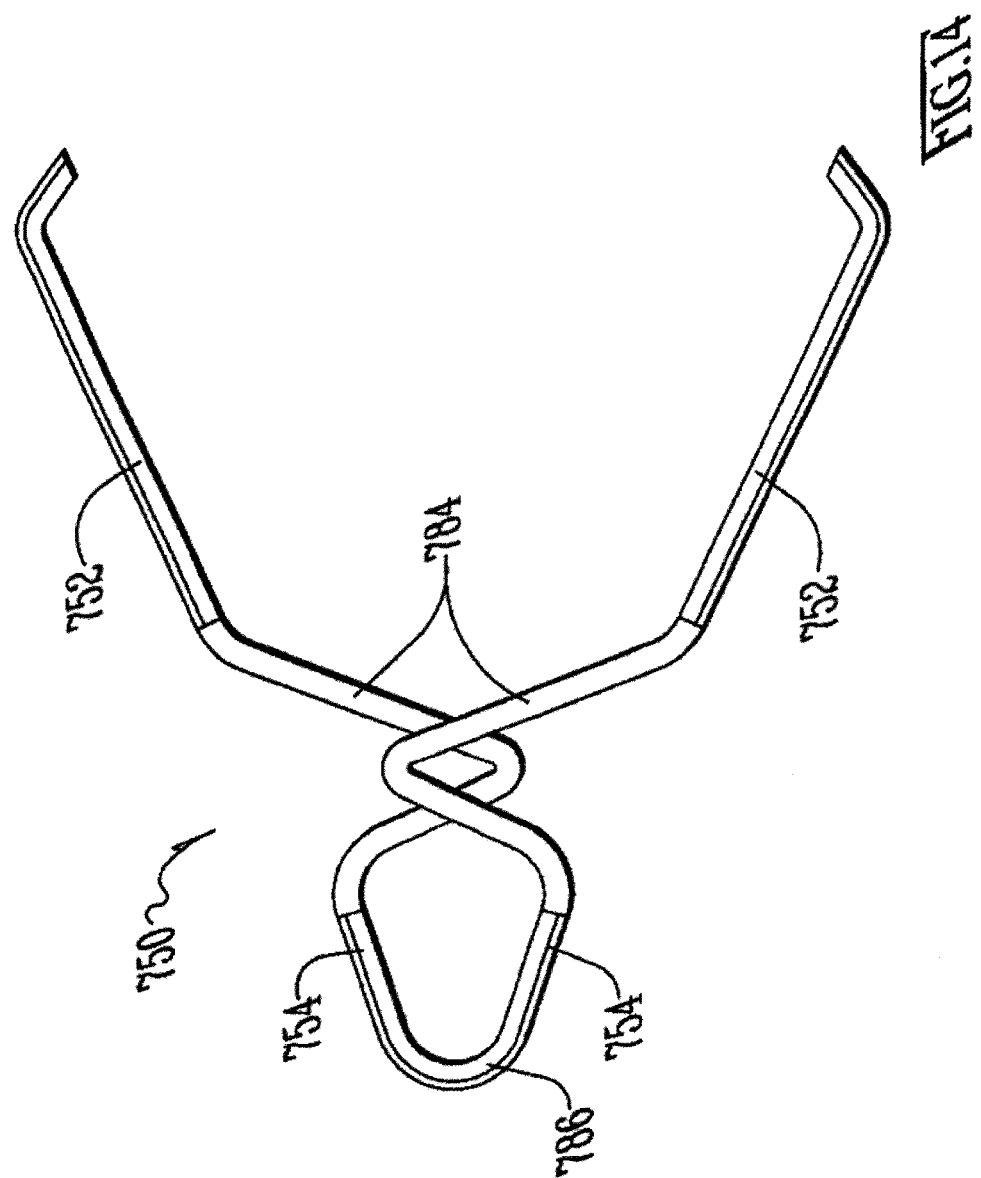

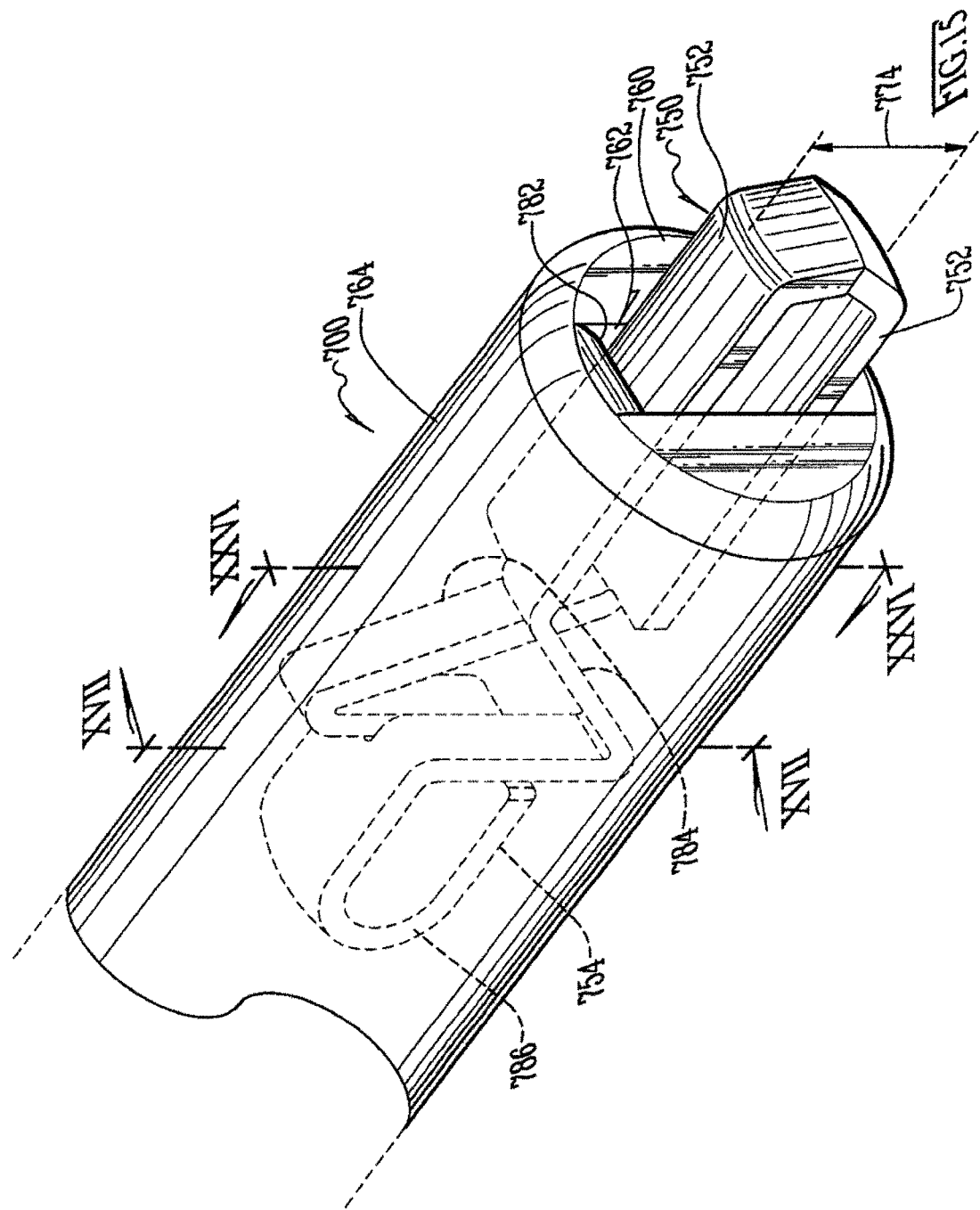

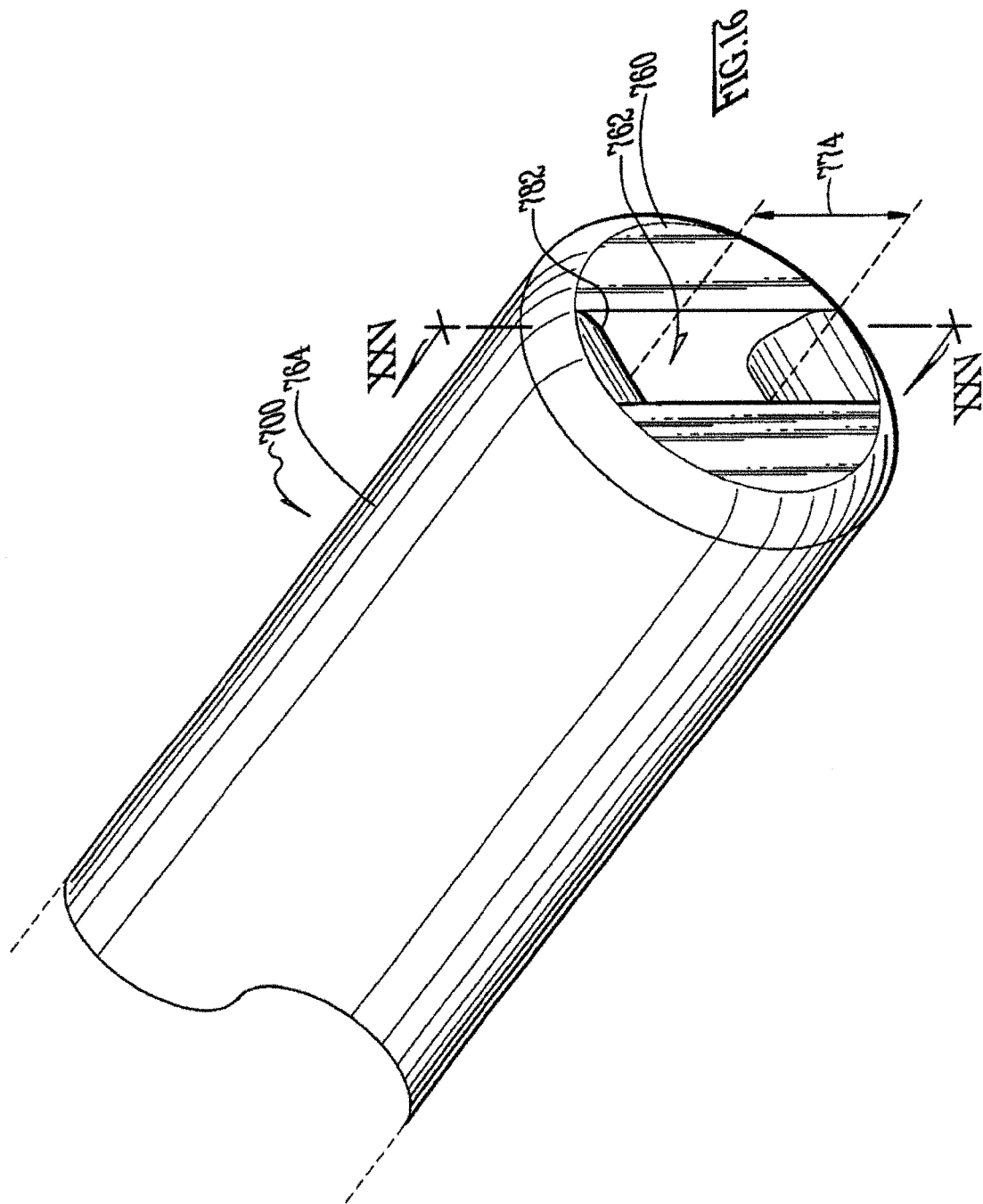

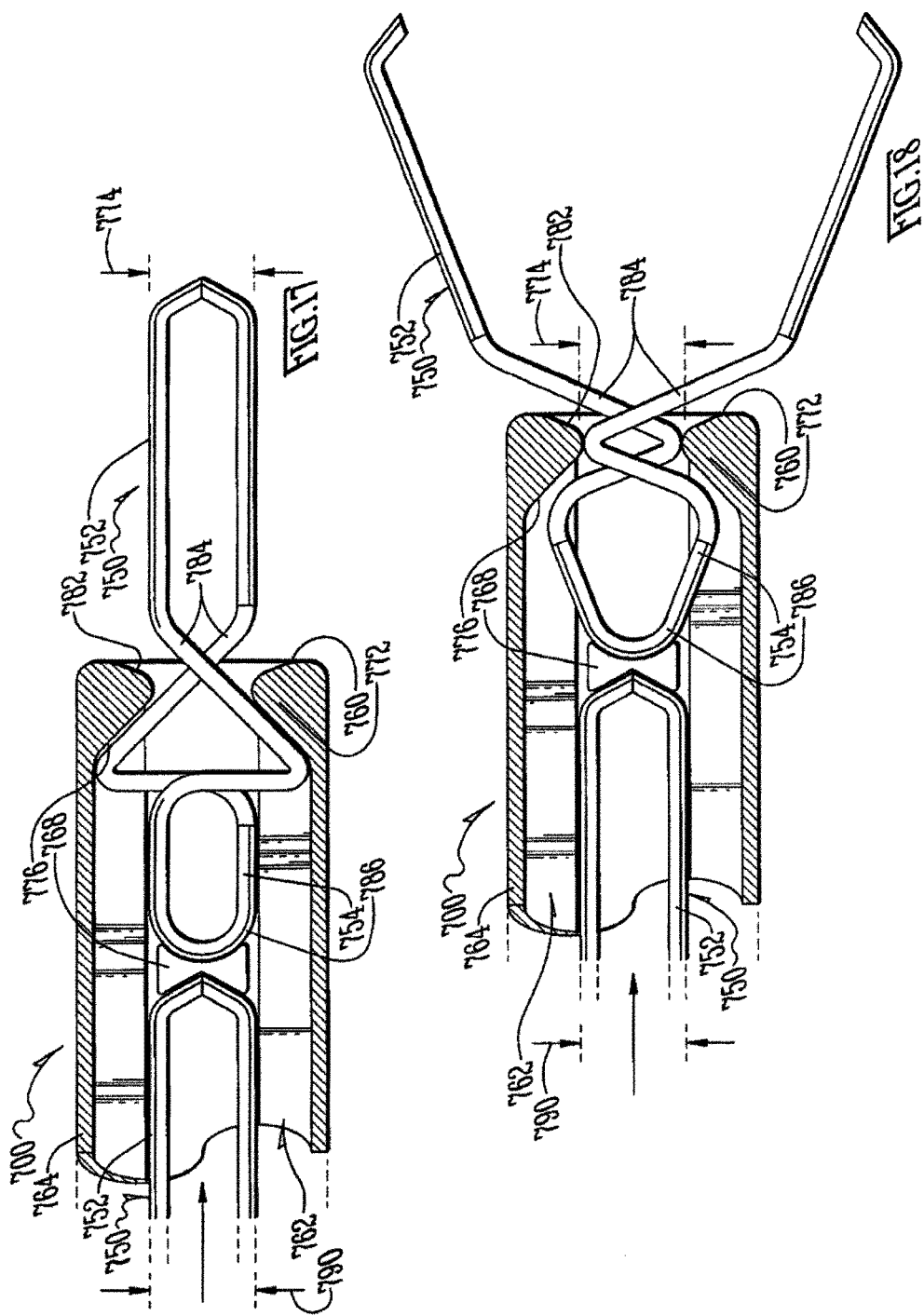

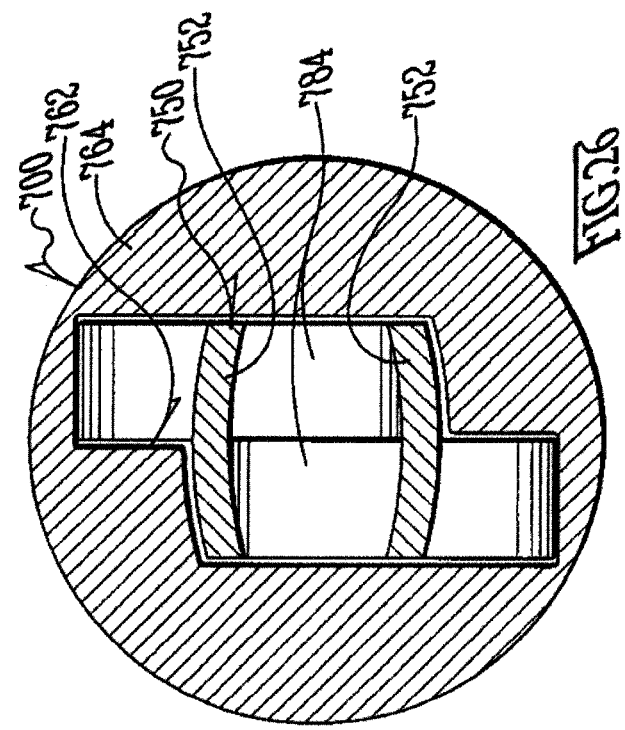
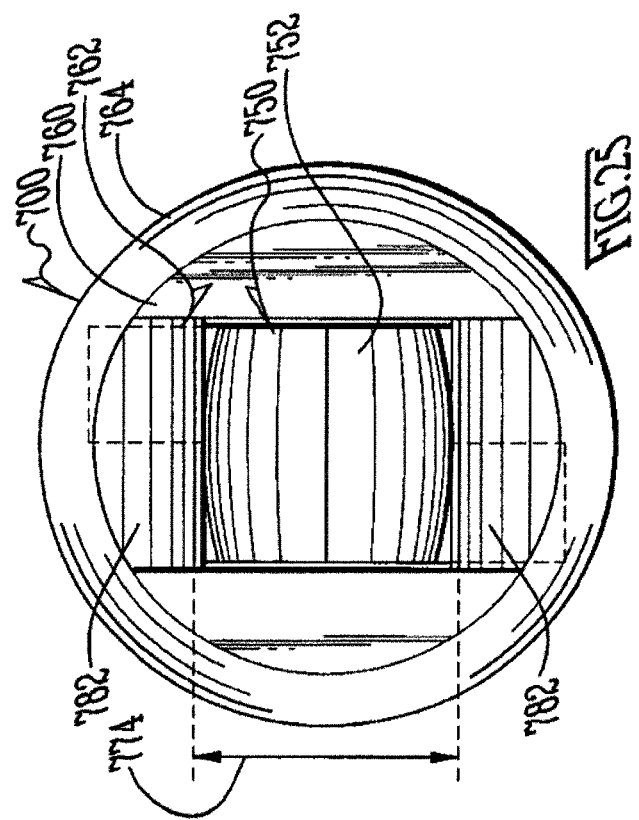

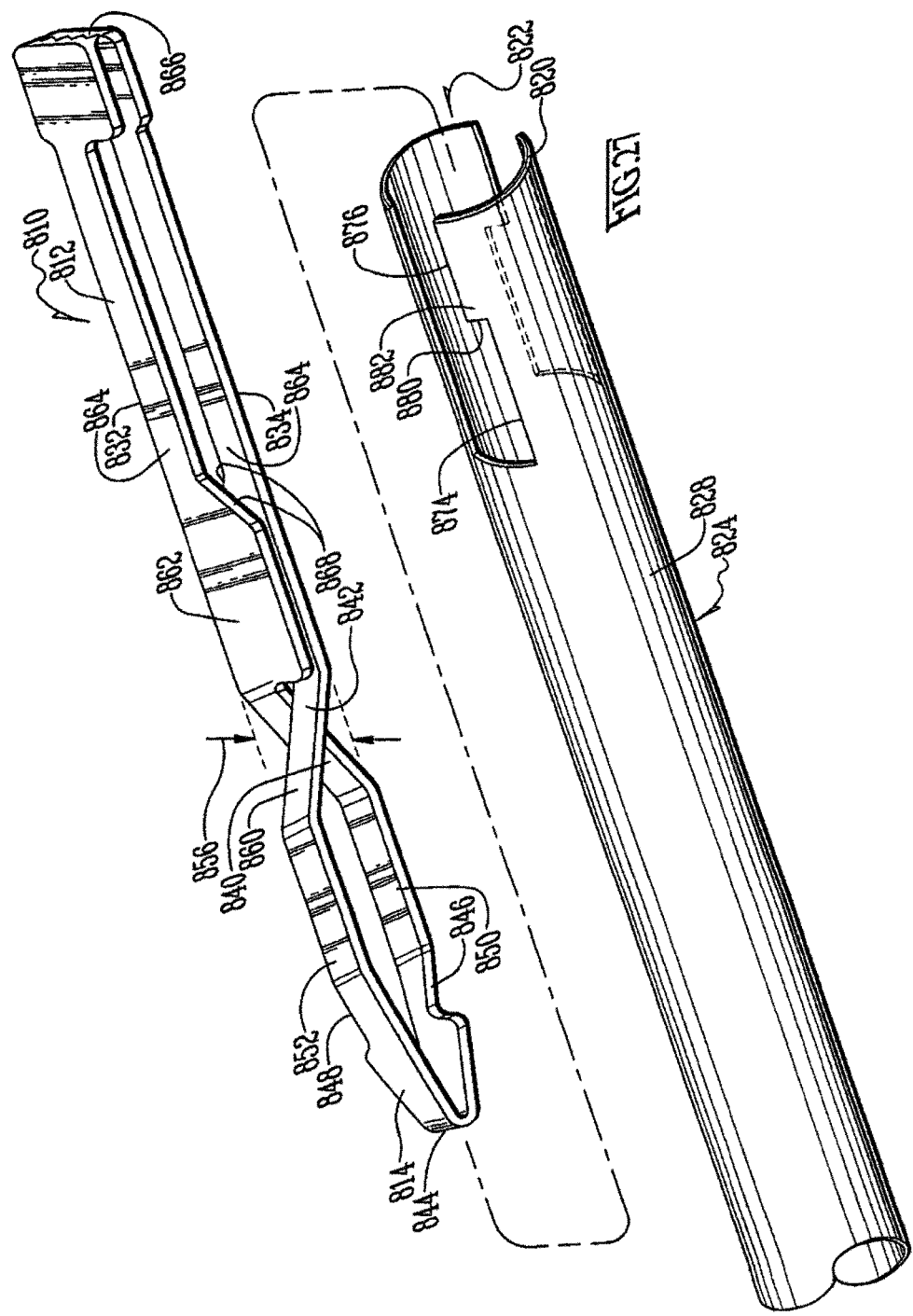

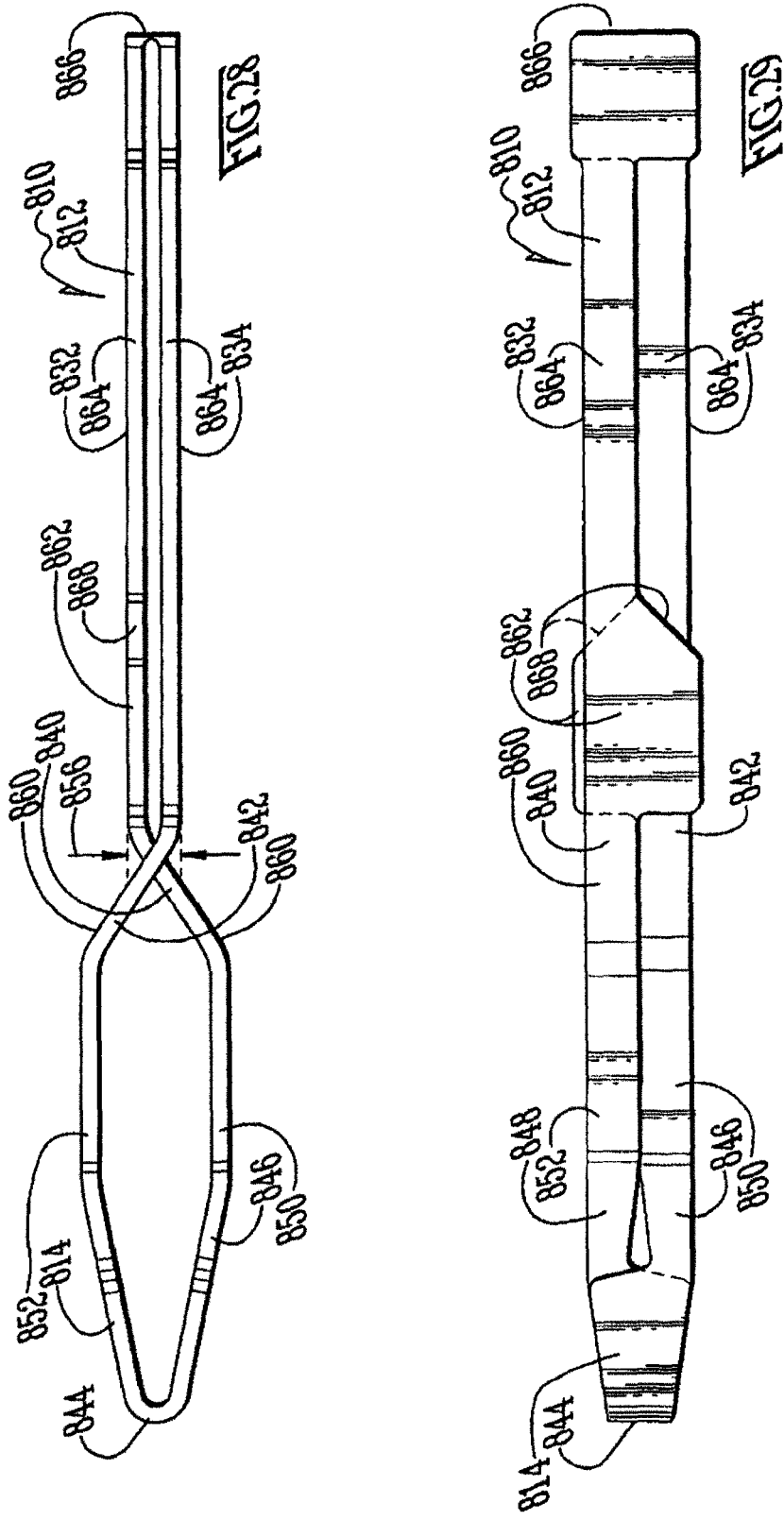

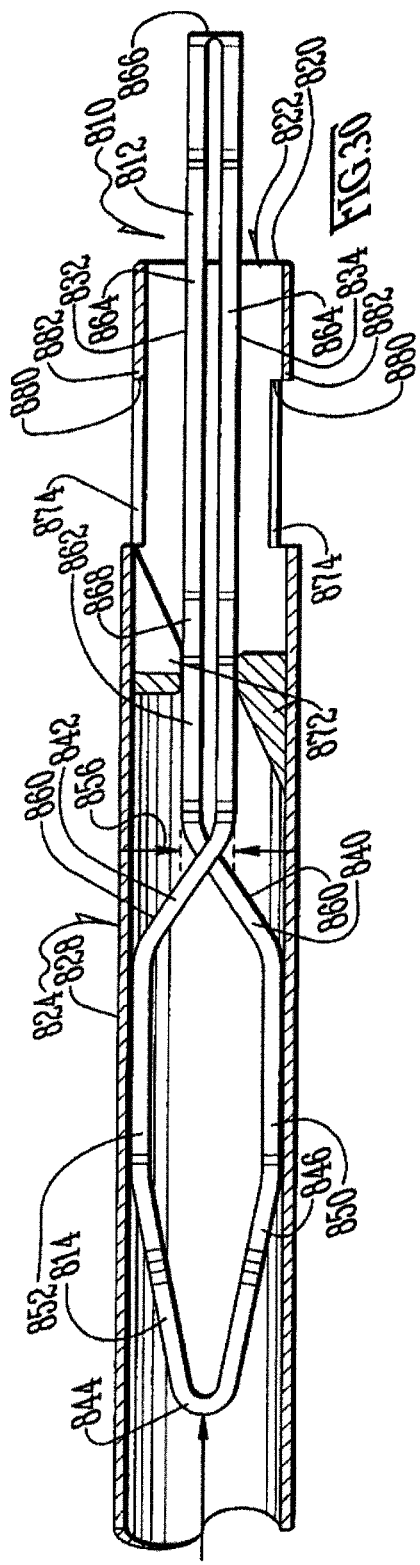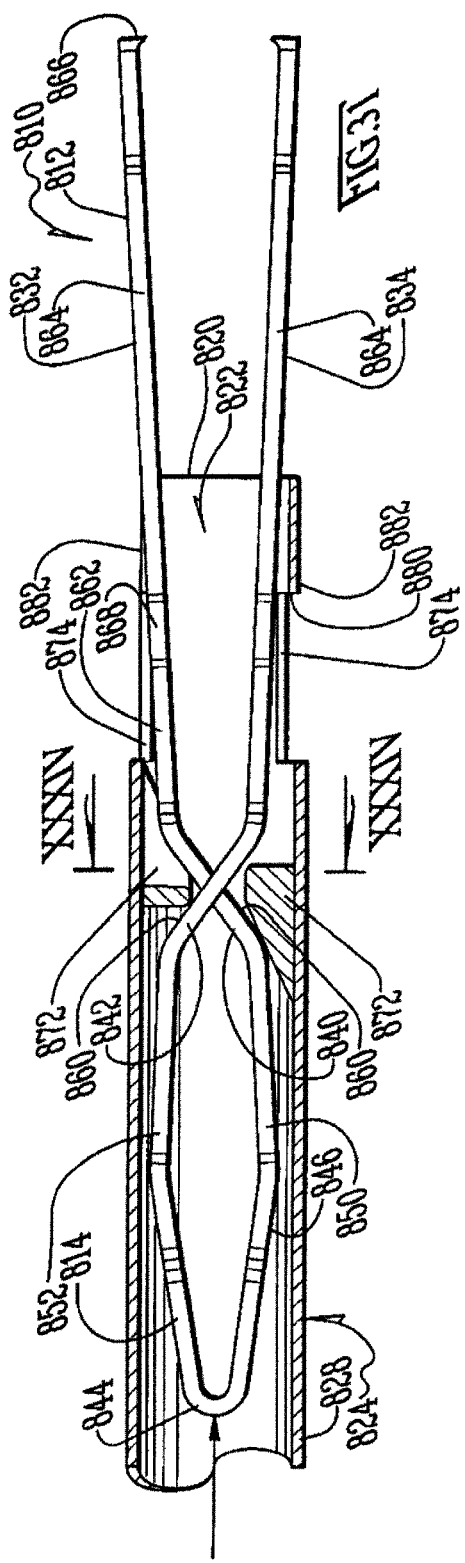

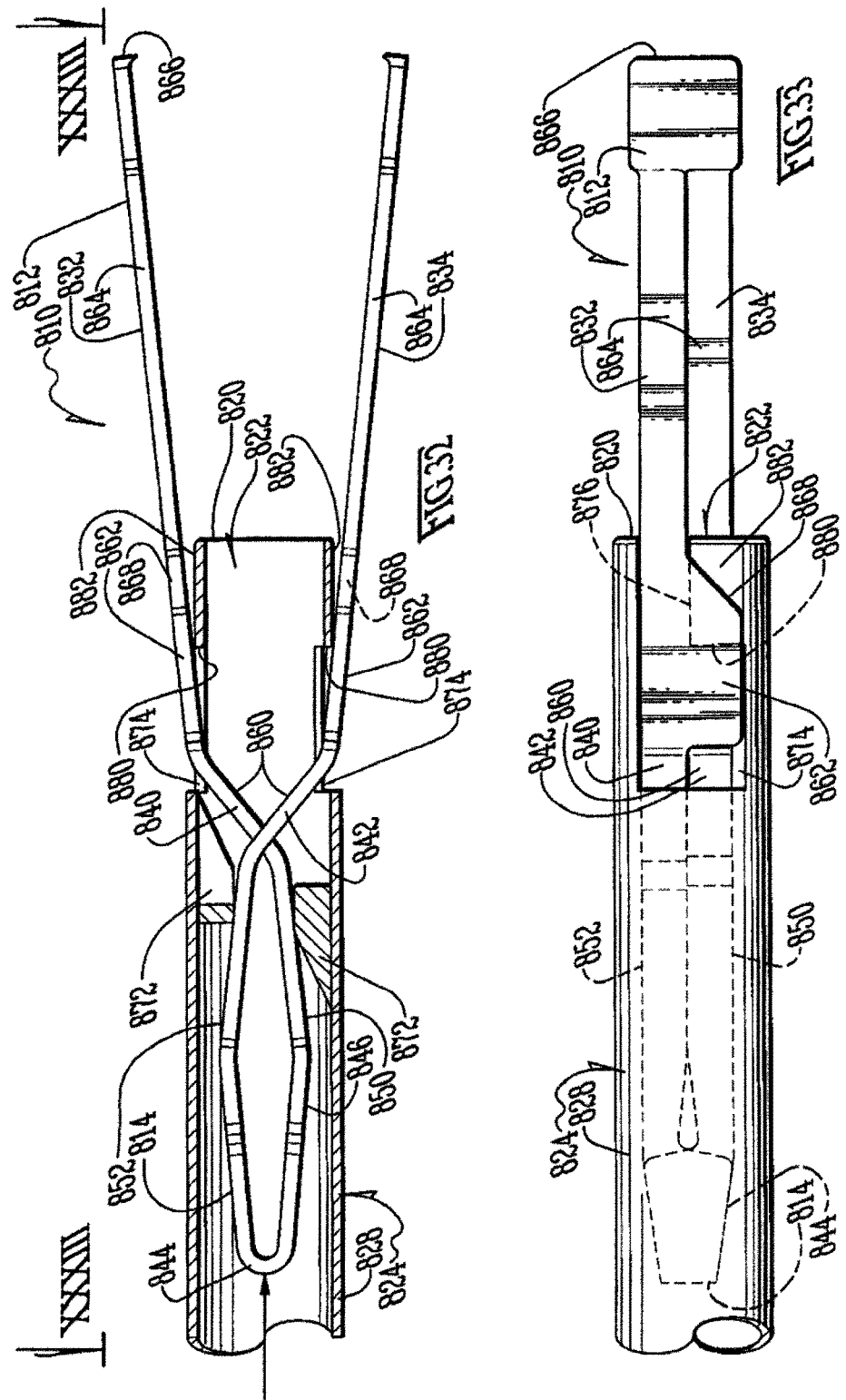

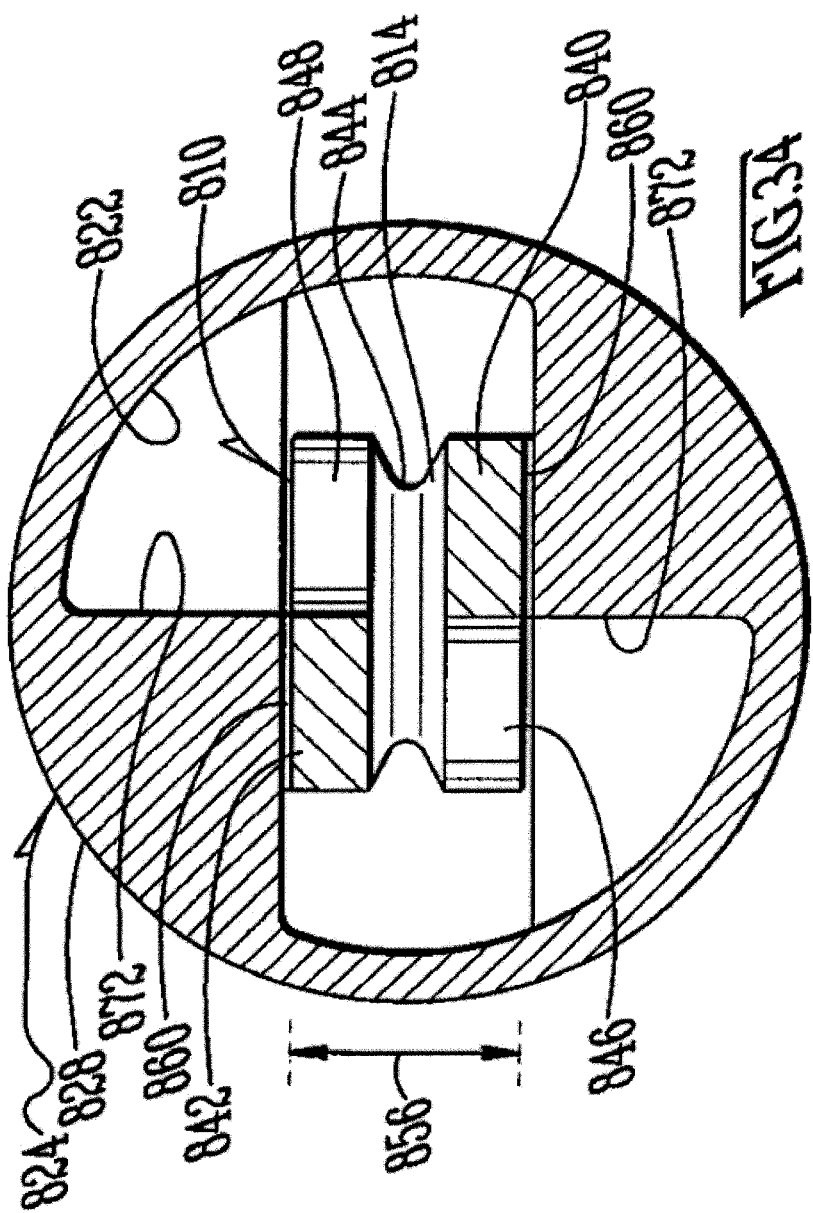

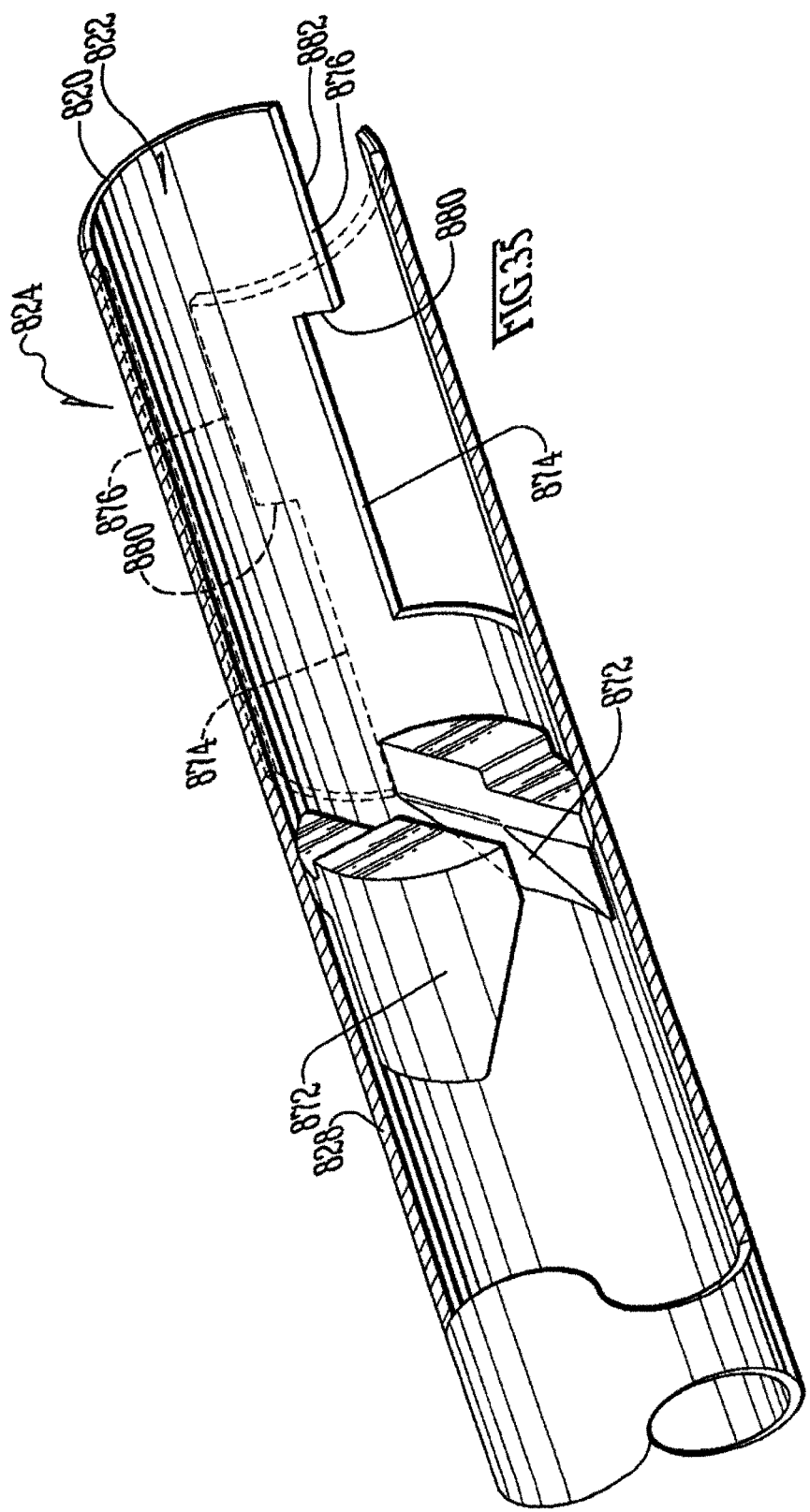

SPRING-CLOSING ENDOSCOPIC CLIP WHERE THE SPRING ACTION CAN ALSO REVERSE THE CLIP PRIOR ANYTIME BEFORE FULL EJECTION

CROSS-REFERENCE TO RELATED APPLICATION(S)

This application claims the benefit of U.S. Provisional Application No. 62/378,390, filed Aug. 23, 2016; U.S. Provisional Application No. 62/291,131, filed Feb. 4, 2016; and U.S. Provisional Application No. 62/236,461, filed Oct. 2, 2015.

This application is a continuation-in-part of U.S. patent application Ser. No. 14/834,186, filed Aug. 24, 2015, which claims the benefit of U.S. Provisional Application No. 62/081,755, filed Nov. 19, 2014, U.S. Provisional Application No. 62/076,149, filed Nov. 6, 2014, U.S. Provisional Application No. 62/073,664, filed Oct. 31, 2014, and U.S. Provisional Application No. 62/040,908, filed Aug. 22, 2014;

and which is also a continuation-in-part of U.S. patent application Ser. No. 14/721,312, filed May 26, 2015, which claims the benefit of U.S. Provisional Application No. 62/002,691, filed May 23, 2014; and U.S. Provisional Application No. 62/016,717, filed Jun. 25, 2014;

and which in turn is a continuation-in-part of U.S. patent application Ser. No. 14/276,513, filed May 13, 2014, which claims the benefit of U.S. Provisional Application No. 61/961,842, filed Oct. 24, 2013; U.S. Provisional Application No. 61/957,306, accorded filing date of Jun. 29, 2013; and, U.S. Provisional Application No. 61/855,313, accorded filing date of May 14, 2013.

The foregoing patent disclosures are incorporated herein by this reference thereto.

BACKGROUND AND SUMMARY OF THE INVENTION

The invention relates to surgery and, more particularly, to endoscopic surgery clips.

It is an object of the invention to provide endoscopic surgery clips with opposed jaws which are driven shut by a spring-biased jaw-clenching provision(s).

It is an additional object of the invention to provide endoscopic surgery clips that have such spring-biased jaw-clenching provision(s) that allow the jaws to open very wide outside the dispensing end of the lumen therefor in the endoscopic catheter.

It is another object of the invention to provide endoscopic surgery clips that have such spring-biased jaw-clenching provision(s) that moreover serve to facilitate reversal of the lead clip to-be-ejected, prior anytime before full ejection past the dispensing end, and at least partially reversed back into the lumen therefor in the endoscopic catheter.

A number of additional features and objects will be apparent in connection with the following discussion of the preferred embodiments and examples with reference to the drawings.

BRIEF DESCRIPTION OF THE DRAWINGS

There are shown in the drawings certain exemplary embodiments of the invention as presently preferred. It should be understood that the invention is not limited to the embodiments disclosed as examples, and is capable of variation within the scope of the skills of a person having ordinary skill in the art to which the invention pertains. In the drawings, FIG. 1 is a perspective view of an endoscopic surgery clip in accordance with the invention having jaws which are driven shut by a spring-biased jaw-clenching provision(s), which spring-biased jaw-clenching provision(s) not only allow the jaws to open very wide outside the dispensing end of the lumen therefor in the endoscopic catheter, but also facilitate the reversal of the lead clip to-be-ejected, prior anytime before full ejection past the dispensing end, and as at least partially reversed back into the lumen therefor in the catheter;

FIG. 2 is a reduced scale side elevation view thereof, wherein jaw lengths of two lengthier lengths are shown in dashed lines;

FIG. 3 is a front elevational view of FIG. 1;

FIG. 4 is a perspective view showing the clip of FIG. 1 loaded into the lumen of a dispensing sleeve of an endoscopic catheter (which is not fully shown here), wherein the clip shown here is disposed in the ejection station of the dispensing sleeve, or the lead clip position if at the head of a series of trailing clips (not shown here, but see FIG. 6) furthermore loaded into the dispensing sleeve;

FIG. 6 is a sectional view taken along line VI-VI in FIG. 4;

FIG. 7 is an enlarged-scale sectional view taken along the line VII-VII in FIG. 5;

FIG. 8 is an enlarged-scale elevational view taken in the direction of arrows VIII-VIII in FIG. 4;

FIG. 9 is a sectional view comparable to FIG. 6 except showing the jaws of the lead clip being spread open outside of the dispensing end of the lumen therefor in the endoscopic catheter;

FIG. 13 is a perspective view of an alternate embodiment of an endoscopic surgery clip in accordance with the invention having jaws which are driven shut by a spring-biased jaw-clenching provision(s), which spring-biased jaw-clenching provision(s) not only allow the jaws to open very wide outside the dispensing end of the lumen therefor in the endoscopic catheter, but also facilitate the reversal (albeit a more limited reversal than the FIGS. 1-12 embodiment) of the lead clip to-be-ejected, prior anytime before full ejection past the dispensing end, and as at least partially reversed back into the lumen therefor in the catheter; wherein, the clip in FIG. 13 is shown in a spread apart state, as if biting into target tissue, except the target tissue is not shown;

FIG. 14 is a side elevation view thereof;

FIG. 15 is a perspective view showing the clip of FIG. 13 loaded into the lumen of a dispensing sleeve of an endoscopic catheter (which is not fully shown here), wherein the clip shown here is disposed in the ejection station of the dispensing sleeve, or the lead clip position if at the head of a series of trailing clips furthermore loaded into the dispensing sleeve;

FIG. 16 is a perspective view comparable to FIG. 15 except with the lead clip removed;

FIG. 17 is a sectional view taken along line XVII-XVII in FIG. 15;

FIG. 18 is a sectional view comparable to FIG. 17 except showing the jaws of the lead clip being spread open outside of the dispensing end of the lumen therefor in the endoscopic catheter;

FIG. 25 is an enlarged-scale elevational view taken in the direction of arrows XXV-XXV in FIG. 16; and FIG. 26 is an enlarged-scale sectional view taken along the line XXVI-XXVI in FIG. 15;

FIG. 27 is a perspective view of a further embodiment of an endoscopic surgery clip in accordance with the invention having jaws which are driven shut by a spring-biased jaw-clenching provision(s), which spring-biased jaw-clenching provision(s) not only allow the jaws to open very wide outside the dispensing end of the lumen therefor in the endoscopic catheter, but also facilitate the reversal of the lead clip to-be-ejected, prior anytime before full ejection past the dispensing end, and as at least partially reversed back into the lumen therefor in the catheter, and further including illustration of the terminal end of dispensing sleeve therefor also in accordance with the invention;

FIG. 28 is a side elevation view of the clip of FIG. 27; and

FIG. 29 is a top plan view of the clip of FIG. 27;

FIG. 30 is a sectional view comparable to any of FIG. 6, FIG. 17 or any of the comparable sectional views which comprise a series of snapshots of progression of the respective clips in the respective dispensing sleeves of FIG. 6 or 17, except this FIG. 30 illustrates the clip and dispensing sleeve of FIG. 27;

FIG. 31 is a sectional view comparable to FIG. 30 except showing the shut jaws of the lead clip being pushed further past the dispensing end of the dispensing sleeve in the endoscopic catheter;

FIG. 32 is a sectional view comparable to FIGS. 30-31 except showing the jaws of the lead clip being spread open outside of the dispensing end of the lumen therefor in dispensing sleeve of the endoscopic catheter, by virtue of the full-width tabs engaging the bearing surface of the shoulder of the L-shaped opening in the dispensing sleeve of the catheter;

FIG. 33 is a top plan view taken in the direction of arrows XXXIII-XXXIII in FIG. 32;

FIG. 34 is an enlarged-scale sectional view taken along the line XXXIV-XXXIV in FIG. 31;

FIG. 35 is a partial sectional view of the dispensing end of the lumen therefor in the dispensing sleeve of the endoscopic catheter.

DETAILED DESCRIPTION OF THE PREFERRED EMBODIMENTS

Figure 5:
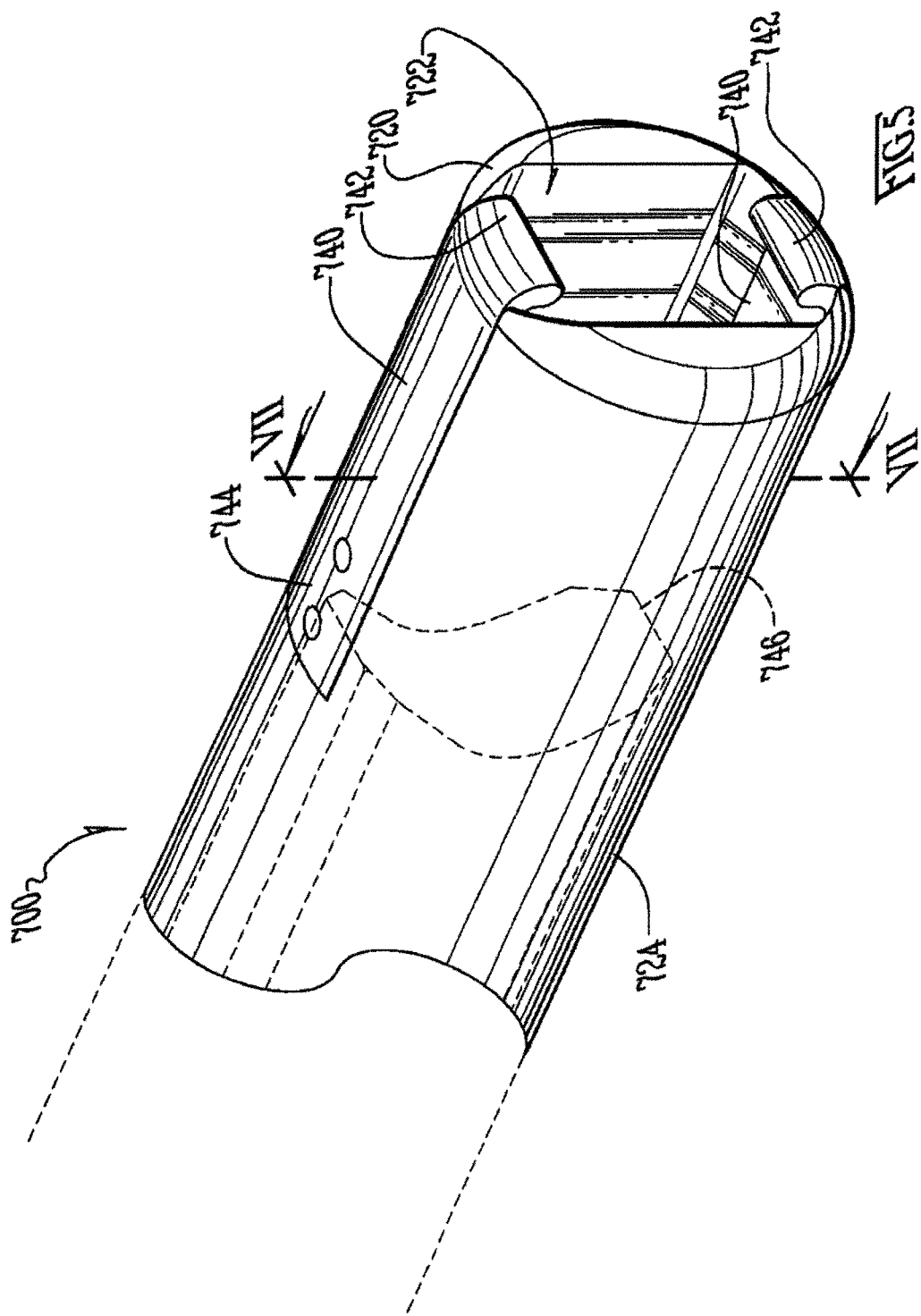
FIG. 5 is a perspective view comparable to FIG. 4 except with the clip removed.

FIGS. 1-12 show a first embodiment of an endoscopic surgery clip 710 in accordance with the invention having jaws 712 which are driven shut by a spring-biased jaw-clenching provision(s) 714, which spring-biased jaw-clenching provision(s) 714 not only allow the jaws 712 to open very wide outside the dispensing end 720 of the lumen 722 therefor in the endoscopic catheter 724, but also facilitate the reversal of the lead clip 710 to-be-ejected, prior anytime before full ejection past the dispensing end 720, and as at least partially reversed back into the lumen 722 therefor in the catheter 724.

The clip 710 comprises a pair of jaws 712 connected together at a resilient tail end 714 (or spring-biased jaw-clenching provision) 714 that flexes the jaws 712 in the shut position as shown in FIGS. 1-4. It is an aspect of the invention that each jaw 712 has a broad outboard side 732 from which projects a forwardly flaring barb 734.

FIGS. 4-12 shows a dispensing apparatus 700 in accordance with the invention for which can be loaded with a multiplicity of clips 710 (see, eg, FIGS. 6 and 9-12) in a straight line series for dispensing the clips 710 serially one at a time.

The dispensing apparatus comprises 700 an elongated flexible catheter 724 formed with a central hollow core or lumen 722 terminating in a dispensing end 720 and loaded with a series of clips 710 in a head (eg., the tip ends of the jaws) to tail fashion.

Projected away from the terminal end 720 of the dispensing apparatus 700 are a pair of resilient spaced arms or grabbers 740. FIGS. 4-8 shows the "at rest" position for the grabbers 740. The grabbers 740 have in-turned reverse-formed barbs 742 at their free ends forming a constriction to the dispensing of the clips 710. The grabbers 740 are elongated from a tail end 744 affixed to the catheter 724 rearward of the dispensing end 720 to a forward end formed with the in-turned reverse-formed barbs 742. The grabbers 740 are produced of a springy resilient material. FIGS. 9-12 shows a series of progressively flexed positions for the lead clip 710 and grabbers 740, wherein FIG. 12 more or less represents the extreme flexed position.

The dispensing apparatus 700 further comprises a manually operated push rod 746 (or -plunger 746, see FIGS. 4-7 and 9-12) for pushing on the tail end 714 of the last clip 710 in the series of such clips 710 loaded into the dispensing apparatus 700. As the plunger 746 pushes on the tail of the last clip 710, that pushing force is transmitted serially through the line of clips 710 until the lead clip 710 is forced through the terminal end 720 of the dispensing apparatus 700.

FIGS. 6 and 9-12 shows the lead clip 710's experience at the terminal end 720. The in-turned reverse-formed barbs 742 of the grabbers 740 form a constriction that catch the forward flaring barbs 734 of the lead clip 710, and flare open the jaws 712 of the lead clip 710. If the manual operator (eg., user, surgeon) of the dispensing apparatus 700 does not like where he or she has aimed the lead clip 710, he or she can ease up on the plunger 746 anywhere between FIGS. 9 and 11, and the resilient arms 740 will force the lead clip 710 in reverse (along with the rest of the series of clips 710), until the lead clip 710 retracts some way back into the lumen 722 of the dispensing apparatus 700, as shown in the position about at FIG. 9.

If on the other hand, the manual operator of the dispensing apparatus is pleased with the aim of the lead clip 710, he or she forces the plunger 746 harder until three things happen. One, the reverse barbs 742 of the arms 740 flare the jaws 712 of the lead clip 710 wider and wider and wider. Two and correspondingly, the widening jaws 712 of the lead clip 710 flare the arms 740 wider and wider and wider apart. And three and ultimately, the reverse barbs 742 of the arms 740 lose purchase on the forward barbs 734 of the lead clip 710, such that, henceforth the lead clip 710 is sprung free and successfully allowed to clamp its jaws 712 on the target tissue. Hence FIG. 12 represents the point-of-no-return for the lead clip 710.

Figure 10:
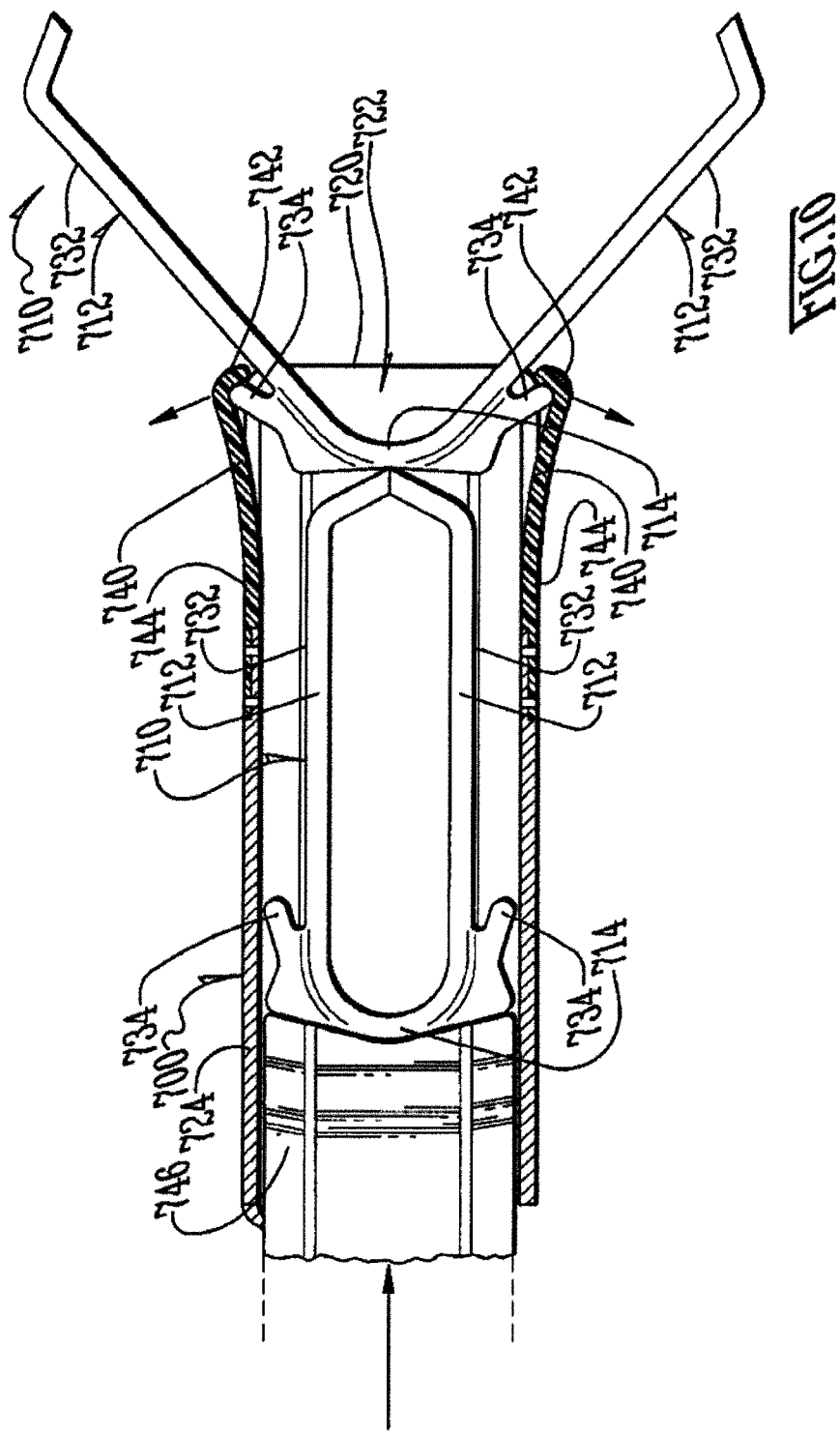
FIG. 10 is a sectional view comparable to FIGS. 6 and 9 except showing the jaws of the lead clip being spread open even wider outside of the dispensing end of the lumen therefor in the endoscopic catheter.
Figure 11:
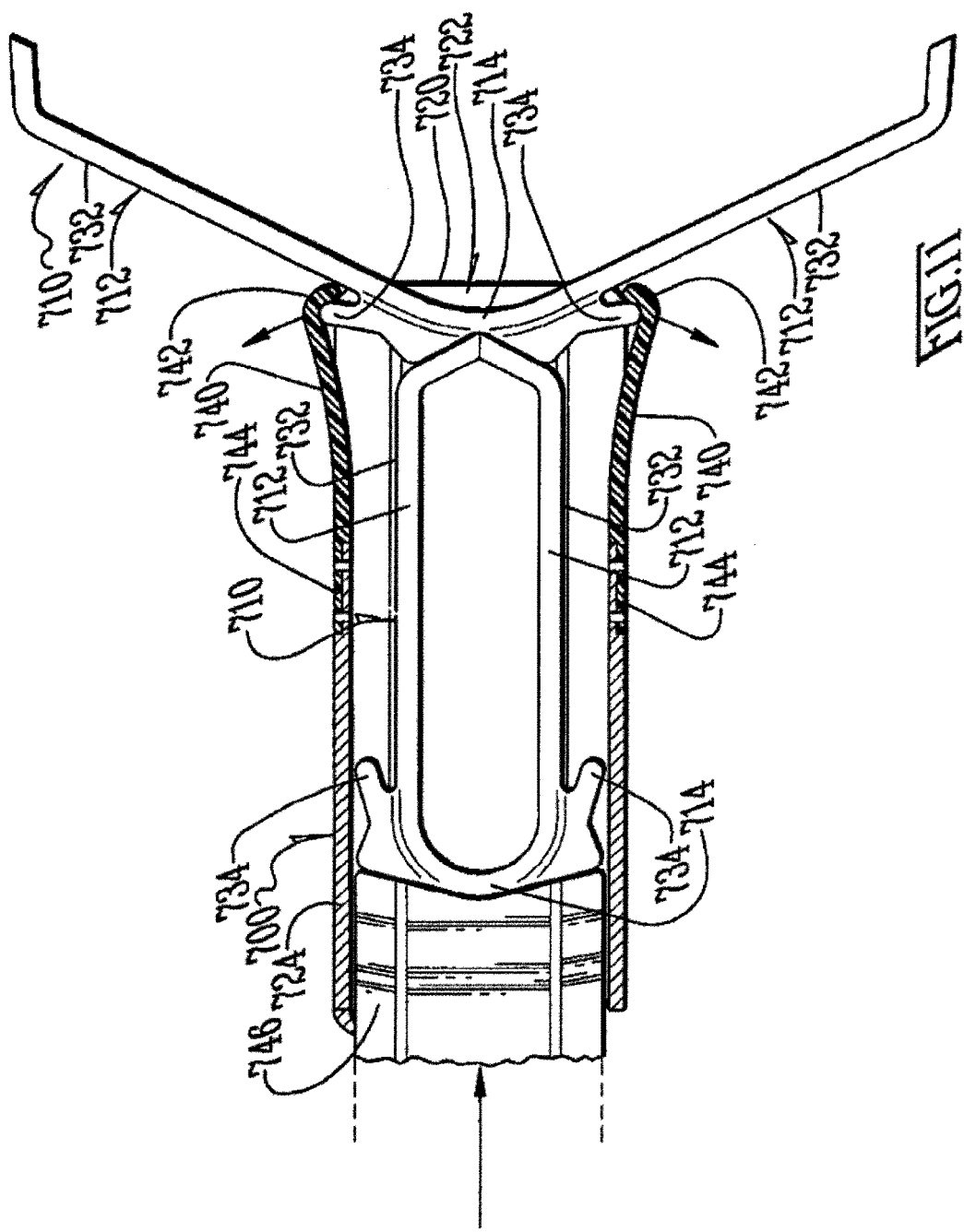
FIG. 11 is a sectional view comparable to FIGS. 6 and 9-10 except showing the jaws of the lead clip being spread open even wider still outside of the dispensing end of the lumen therefor in the endoscopic catheter.
Figure 12:
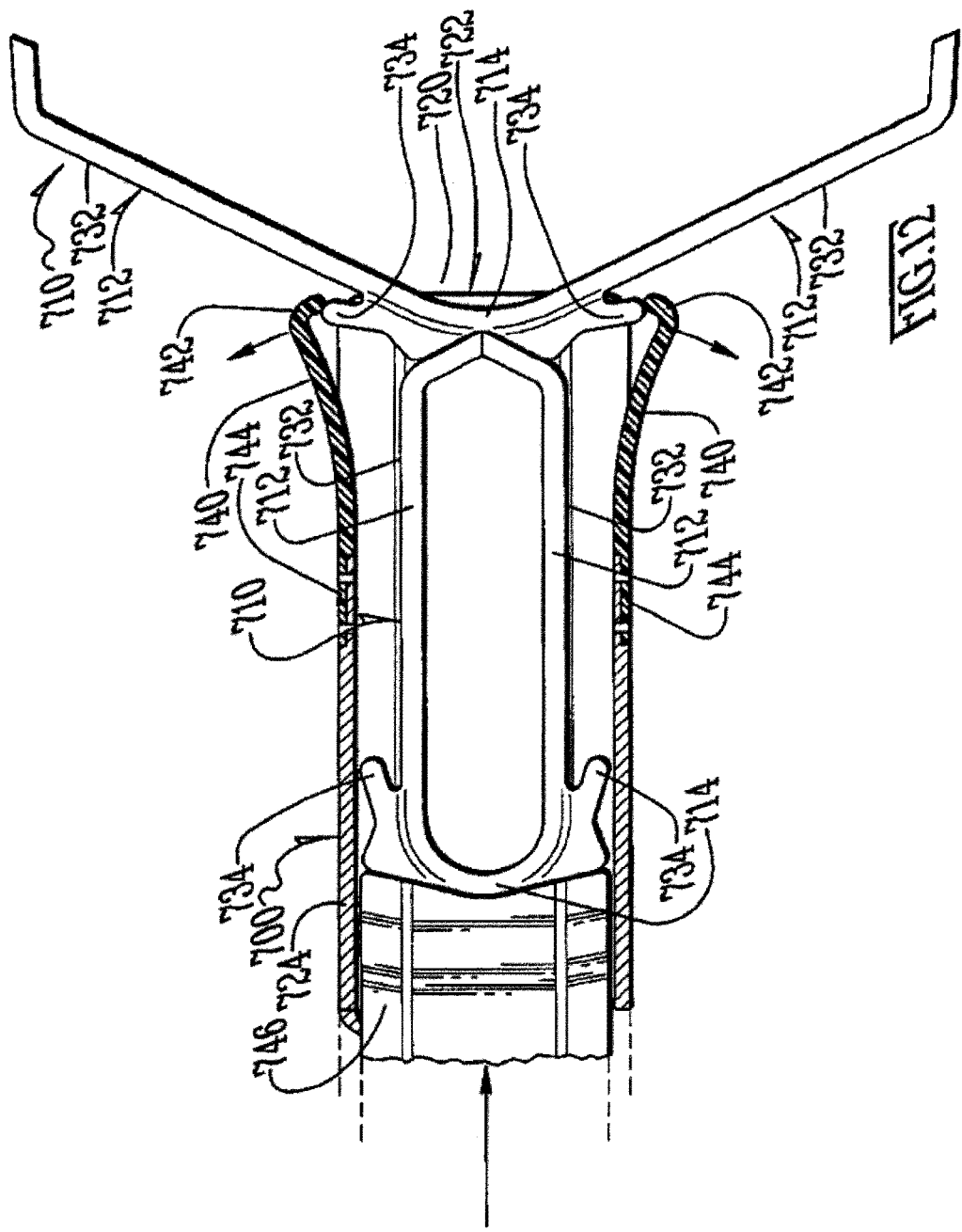
FIG. 12 is a sectional view comparable to FIGS. 6 and 9-11 except showing the lead clip being dispensed past the point-of-no-return relative the dispensing end of the lumen therefor in the endoscopic catheter; wherein for any position of the lead clip in FIGS. 9-11, if the forward position of the forwardly-urging plunger is reversed any at all, the spring-clenching provision(s) of the lead clip will force the lead clip to reverse (or retreat) back into the lumen therefor, shutting the jaws to the relative state of closure shown by about FIG. 9, more or less.

Again, FIG. 12 shows the lead clip 710 being dispensed past the point-of-no-return relative the dispensing end 720 of the lumen 722 therefor in the endoscopic catheter 724; wherein for any position of the lead clip 710 in FIGS. 9-11, if the forward position of the forwardly-urging plunger 746 is reversed any at all, the spring-clenching provision(s) 714 of the lead clip 710 will force the lead clip 710 to reverse (or retreat) back into the lumen 722 therefor, shutting the jaws 712 to the relative state of closure shown by about FIG. 9, more or less.

The process is repeatable with the succeeding clip 710, and so on, until the last of all the clips 710 in the series are dispensed.

Figure 22:
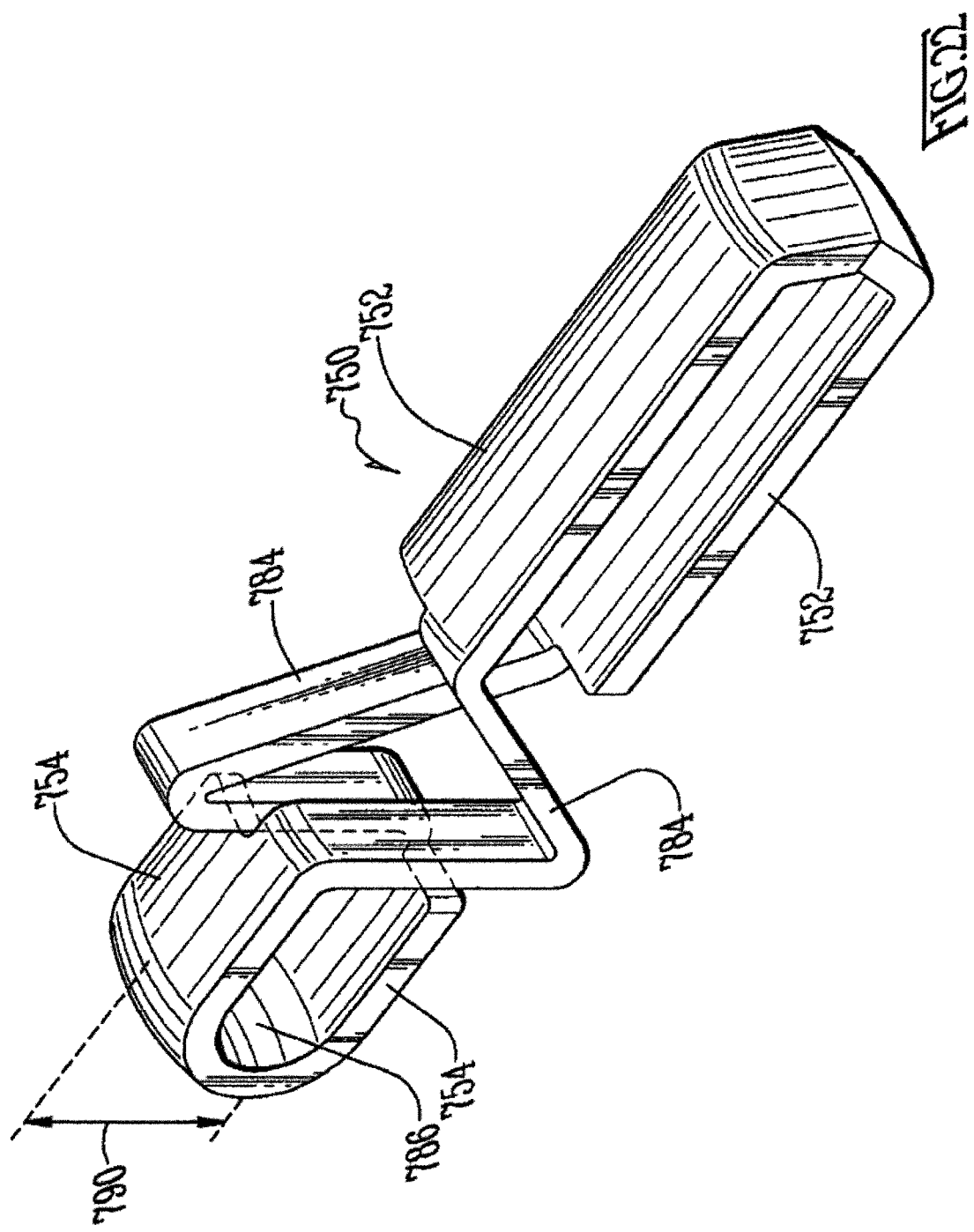
FIG. 22 is a perspective view comparable to FIG. 13 except showing the clip in a completely forced shut state as forced by the spring-biased jaw-clenching-provision(s) therefor.
Figure 23:
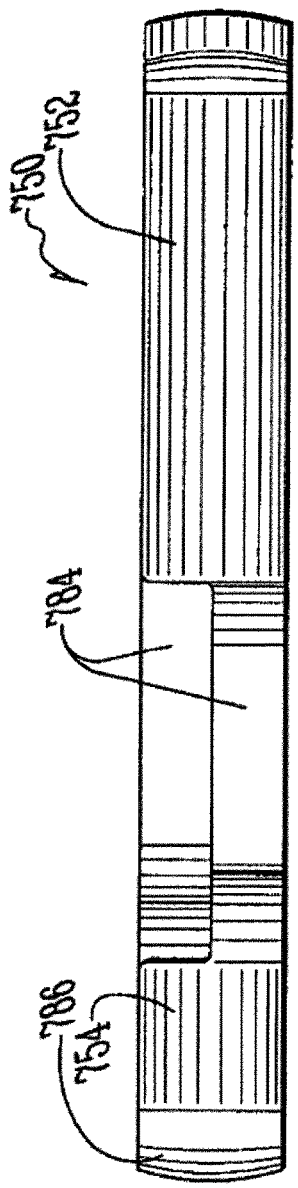
FIG. 23 is a top plan view thereof.
Figure 24:
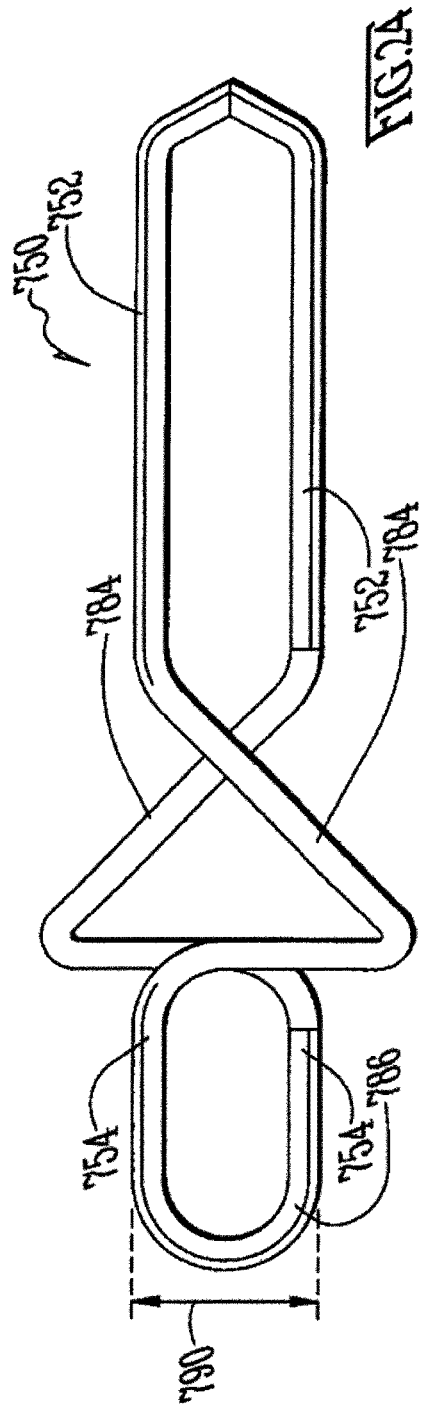
FIG. 24 is a side elevational view thereof.

FIGS. 13-26 show an alternate embodiment of an endoscopic surgery clip 750 in accordance with the invention having jaws 752 which are driven shut by a spring-biased clenching provision(s) 754, which spring-biased jaw-clenching provision(s) 754 not only allow the jaws 752 to open very wide outside the dispensing end 760 of the lumen 762 therefor in the endoscopic catheter 764, but also facilitate the reversal (albeit a more limited reversal than the FIGS. 1-12 embodiment) of the lead clip 750 to-be-ejected, prior anytime before full ejection past the dispensing end 760, and as at least partially reversed back into the lumen 762 therefor in the catheter 764. The clip 750 shown in FIGS. 13 and 14 is shown in a spread apart state, as if biting into target tissue, except the target tissue is not shown. FIGS. 22-24 show the clip 750 in a closed shut state, wherein there is nothing forcing the spreading apart of the jaws 752.

FIG. 15 shows the clip 750 of FIG. 13 loaded into the lumen 762 of an endoscopic catheter 764. The clip 750 shown here is disposed in the ejection station of the endoscopic catheter 764, or the lead clip 750 position if at the head of a series of trailing clips 750 furthermore loaded into the endoscopic catheter 764. This is shown in FIGS. 17-21. The clips 750 are spaced by inter-clip spacers 768.

FIGS. 16-21 and 25 show that the dispensing end 760 is formed with opposed constrictions 772 defining a rectangular passageway 774 between the opposed constrictions 772. The constrictions 772 are formed by a V-shaped funnel surface 776 that presents itself to the clips 750 as the lead clip 750 is forced past. The funnel surface 776 narrows to the rectangular opening 774 (see FIG. 25) as delimited by the opposed constrictions 772 and opposed sidewalls. In the dispensing direction, the constrictions 772 then have a flaring surface 782 past the constriction opening 774.

FIG. 17 shows that the lead clip 750 has figure-8 shaped tail end 754, wherein the leading loop 784 of the figure-8 shaped tail end 754 is tapered to engage the V-shaped funnel surface 776, and the trailing loop 786 is circular to oval but of reduced profile so as to fit through the opening 774 of the v-shaped funnel surface 776. The figure-8 shaped tail end 754 serves as the spring-biased jaw-clenching provision 754 for the clip 750, to clamp the jaws 752 shut as shown in FIGS. 22 and 24.

Figure 19:
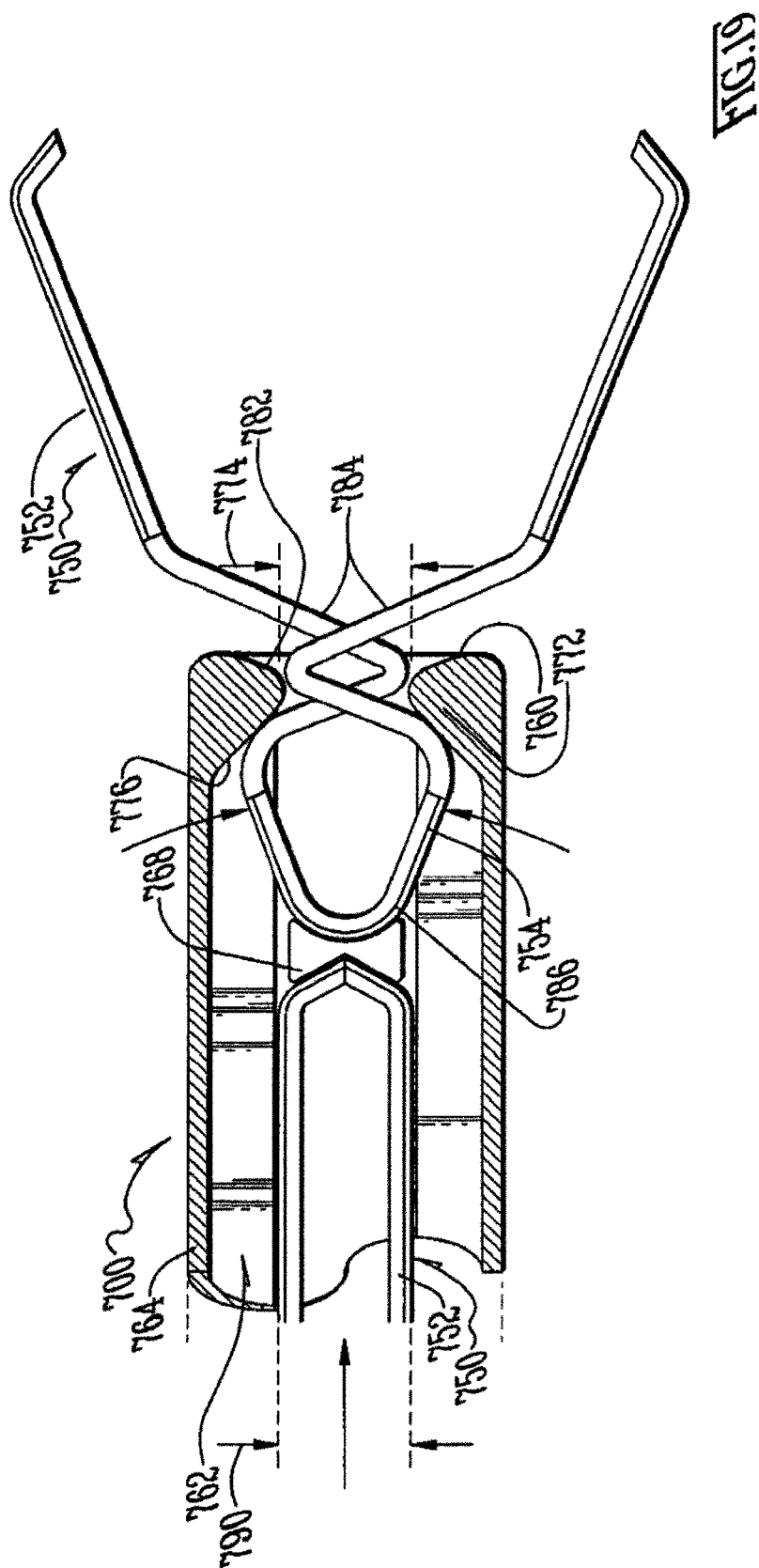
FIG. 19 is a sectional view comparable to FIGS. 17 and 18 except showing the jaws of the lead clip being spread open even wider outside of the dispensing end of the lumen therefor in the endoscopic catheter.
Figure 20:
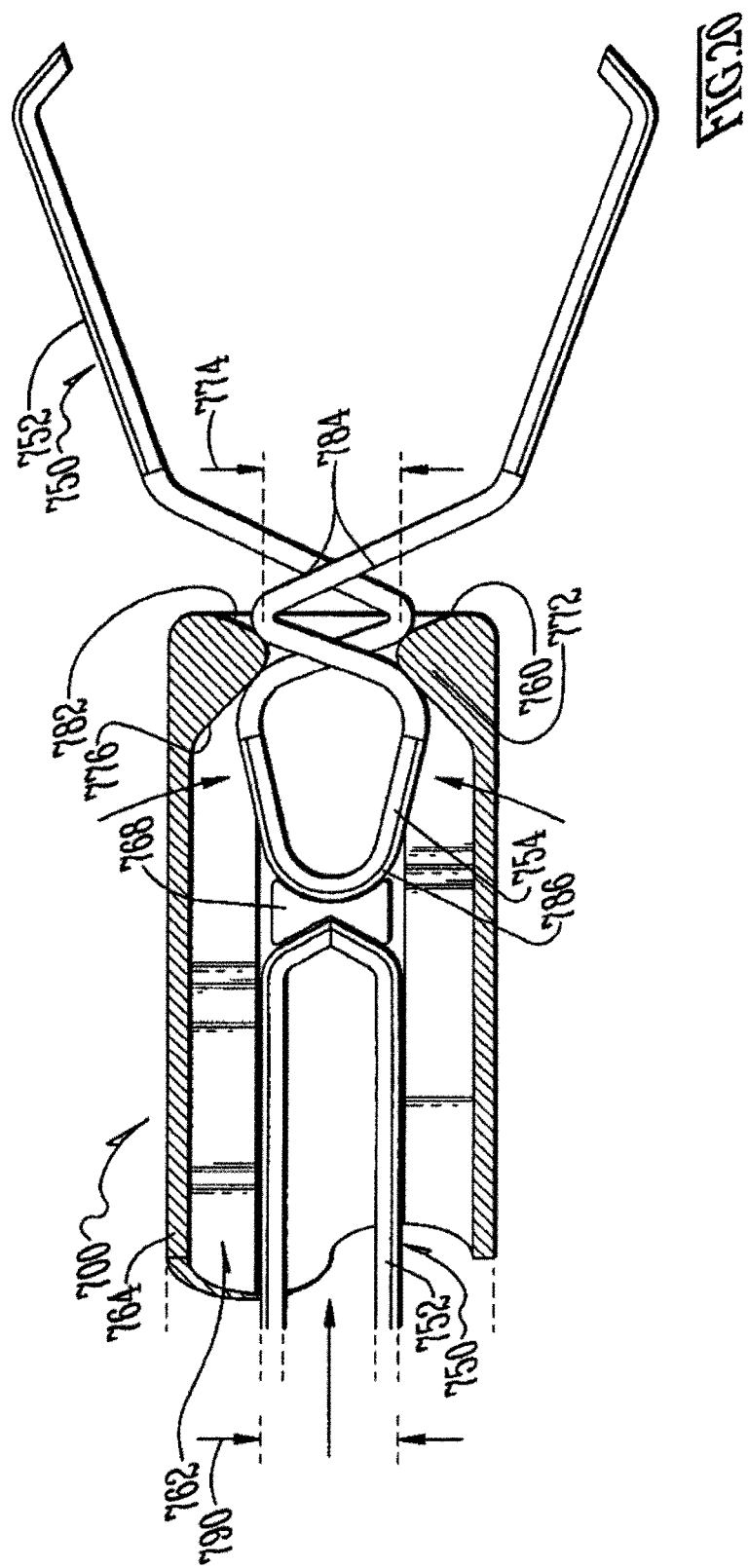
FIG. 20 is a sectional view comparable to FIGS. 17-19 except showing the lead clip being dispensed to a position where it can be stably held by the rectangular constriction of the dispensing end of the dispensing sleeve in the open position as shown, whereby the jaws can be wielded about in three dimensions while the jaws remain open as shown the clip remains in this ejection as shown so long as no more forward push is given by the trailing plunger (not shown, but pushing on the rearmost clip of the series of clips loaded in the lumen of the dispensing sleeve of the endoscopic catheter)

FIG. 18 shows the jaws 752 of the lead clip 750 being spread open outside of the dispensing end 760 of the lumen 762 therefor in the endoscopic catheter 764. FIG. 19 shows the jaws 752 of the lead clip 750 being spread open even wider outside of the dispensing end 760 of the lumen 762 therefor in the endoscopic catheter 764. FIG. 20 shows the lead clip 750 dispensed to a position where it can be stably held by the opposed constrictions 772 of the dispensing end 760 in the open position as shown. That way, the jaws 752 can be wielded about in three dimensions while the jaws 752 remain open as shown the clip 750 remains in this ejection as shown so long as no more forward push is given by the trailing plunger (not shown, but pushing on the rearmost clip 750 of the series of clips 750 loaded in the lumen 762 of the endoscopic catheter 764). The figure-8 shaped tail end 754 of the clip 750 is caught and pinched between the opposed constrictions 772 at the waist 790 of the figure-8 shaped tail end 754. That is, at the waist 790 between the forward loop 784 and trailing loop 786 of the figure-8 shaped tail end 754.

Figure 21:
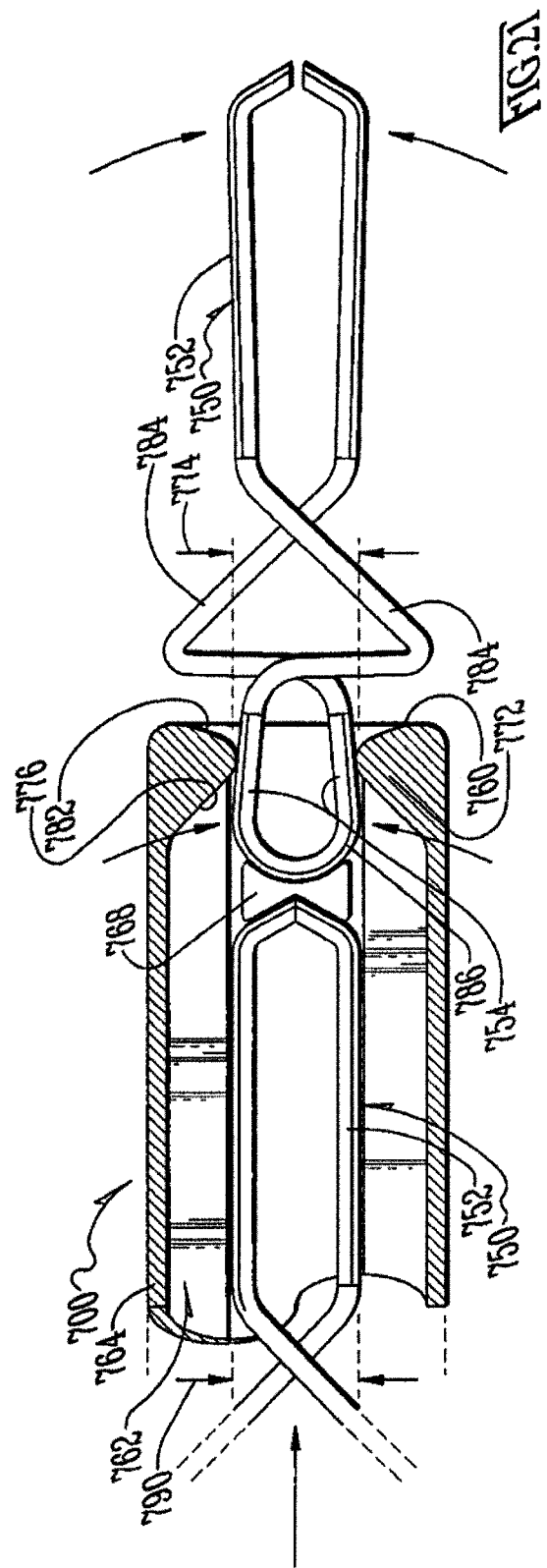
FIG. 21 is a sectional view comparable to FIGS. 17-20 except showing the lead clip being dispensed past the point-of-no-return relative the dispensing end of the lumen therefor in the endoscopic catheter.

FIG. 21 shows the lead clip 750 being dispensed past the point-of-no-return relative the dispensing end 760 of the lumen 762 therefor in the endoscopic catheter 764.

Once again, FIGS. 13-26 show an alternate embodiment of an endoscopic surgery clip 750 in accordance with the invention. The clip 750 has a pair jaws 752 and a rear, spring-biased figure-8 formation 754 serving as the jaw-clenching provisions 754 for this clip 750. The rear figure-8 formation 754 comprises a forward compression loop 784 and a trailing torsion spring loop 786 of the rear figure-8 formation 754 of the clip 750.

FIGS. 17-21 show a lead clip 750, an inter-clip spacer 768, and a trailing clip 750 loaded into a multi-clip dispensing apparatus 700 in accordance with the invention. FIGS. 17-21 show the jaws 752 of the lead clip 750 being flared open by means of in-turned pinching or constriction formations 772 of the dispensing end 760 of the multi-clip dispensing apparatus 700 in accordance with the invention bearing on (and thereby applying compressive pressure on) either the forward compression loop 784 or the trailing torsion spring loop 786 of the rear figure-8 formation 754 of the clip 750.

FIG. 20 shows the lead clip 750 at equilibrium in a static flared open position by virtue of the pinching or constriction formations 772 of the dispensing end 760 of the multi-clip dispensing apparatus 700 in accordance with the invention. The lead clip 750 is caught by the pinching or constricting formations 772 between the forward compression loop 784 of the clip 750 and the trailing torsion spring loop 786 of the rear figure-8 formation 754 of the clip 750.

FIG. 21 is a side view comparable to FIG. 20 except showing the incremental further forward travel of the lead clip 750 out of the dispensing end 760 of the multi-clip dispensing apparatus 700, such that the lead clip 750 has traveled past a point-of-no-return, and is hence ejected to clamp onto target tissue (not shown). The forward compression loop 784 of the clip 750 has traveled past the pinching or constriction formations 772 of the dispensing end 760 of the multi-clip dispensing apparatus 700, and indeed the jaws 752 have swung shut. The trailing torsion spring loop 786 of the clip 750 is in the process being slid between and through said same pinching or constriction formations 772. The lead clip 750 is more or less ejected past this point. The jaws 752 have presumptively clamped down on target tissue. Any relative movement of the catheter 764 will wag the dispensing end 760 sufficient such that the trailing torsion spring loop 786 of the rear figure-8 formation 754 of the clip 750 is dragged out and free from the catheter 764.

FIGS. 27-35 show a further embodiment of an endoscopic surgery clip 810 in accordance with the invention having jaws 812 which are driven shut by a spring-biased jaw-clenching provision(s) 814, which spring-biased jaw-clenching provision(s) 814 not only allow the jaws 812 to open very wide outside the dispensing end 820 of the lumen 822 therefor in the endoscopic catheter 824, but also facilitate the reversal of the lead clip 810 to-be-ejected, prior anytime before full ejection past the dispensing end 820, and as at least partially reversed back into the lumen 822 therefor in the catheter 824. FIG. 27 further includes illustration of the terminal end 820 of dispensing sleeve 828 therefor also in accordance with the invention.

The clip 810 of this embodiment resembles a pair of tweezers except having a trailing spring-biased torsion loop 814 serving as the spring-biased jaw-clenching provision 814.

The surgery clip 810 not only resembles a pair of tweezers except with a trailing spring-biased torsion loop 814, it is bi-laterally symmetric with a left side 832 and right side 834 which move in parallel planes relative to each other, and past each other at a cross-over formation 840, 842.

The surgery clip 810 comprises:
fulcrum end 844, more or less full width of the clip 810,
a left arm 846 and right arm 848 growing out of the fulcrum end 844,
the left and right arms 846 and 848 having rear half loop portions 850 and 852,
which rear half loop portions 850 and 852:
  are slender and span less than half full width of the clip 810,
  have forward ends 840 and 842 defining cross-over sections 840,842,
  define a waist 856 for the clip 810, and
  have outer surfaces 860 defining a spaced pair of compressive cam surfaces 860,
the cross-over sections 840,842 travel aside each other in spaced parallel planes,
the left and right arms 846 and 848 having forward half loop portions 812,
which forward half loop portions 812 comprise the jaws 812 and:
  grow out of the cross-over sections 840,842,
  respectively begin with rear, full-width tab portions 862,
  return to slender less than half-width forward portions 864,
  terminate in full width jaw ends, or teeth 866,
  wherein the tab portions 862 define a spaced pair of spreading cam surfaces 868.

FIGS. 27 and 30-35 show a clip dispensing tube 828 in accordance with the invention for dispensing the clip 810 of FIGS. 27-34.

The dispensing tube 828 comprises proximate the end 820 thereof:
a diametrically spaced pair of L-shaped openings 874, 876, and rearward of them,
left side and right side interior ramp constrictions 872 for compression.

Each of the L-shaped openings 874,876 comprises:
a full-width closed end 874 to allow egress for the tab portions 862,
a half-width slot 876 originating in the closed end 874 and extending to an opening in the dispensing end 820 of the dispensing sleeve 828 of the catheter 824,
wherein the half-width slot 876 first allows egress of the half-width portions of the forward sections 864 of the jaws 812, as well as return egress of the half-width cross-over sections 840,842.

The intersection between the full-width closed end 874 of the L-shaped opening 874,876 and the half-width slot portion 876 of the L-shaped opening 874,876 leave behind a solid shoulder 880 in the dispensing sleeve 828. The half-width slot 876 is defined between a pair of opposed, spreading bearing surfaces 882.

As the clip 810 is pushed out past the interior compression ramps 872, and past through the end 820 of the dispensing sleeve 828, the following happens:
the full-width jaw ends 866 are biased shut,
the shut full-width jaw ends 866 travel between the interior compression ramps 872, and ultimately out the dispensing end 820 of sleeve 828,
the interior compression ramps 872 engage the exterior compression surfaces of 860 the cross over sections 840,842,
this spreads open the half-width forward sections 864 of the jaws 812 which egress through the half-width open slot sections 876 of the L-shaped opening 874,876,
soon after, the spreading cam surfaces 868 of the full-width tabs 862 engage the solid shoulder 880 of the L-shaped openings 874,876,
this ultimately spreads the jaws 812, and jaw ends 866, to their ultimate spread open extreme,
after that, the trailing ends of the full-width tabs 862 ride on the spreading bearing surfaces 882 (ie., the side walls of the half-width open slot portions 876 of the L-shaped opening 874,876),
once the trailing ends of the full-width wedge portions 862 clear the end 820 of the dispensing sleeve 828 of the catheter 824, the jaws 812 (and jaw ends 866) are free to swing shut, due to the spring-biased clenching provision 814 that is the torsion loop end 814 of the clip 810, because the half-width portions 840,842 and 850, 852 of the torsion loop end 814 are free to return egress through the half-width open slot portions 876 of the L-shaped opening 874,876, and because the full-width fulcrum 844 can travel between the interior compression restrictions 872, just as did the shut jaw ends 866.

Once the trailing ends of the full-width tab portions 862 clear past the dispensing end 820 of the dispensing sleeve 828, the resilient fulcrum 844 forces the jaws 812 (and jaw ends 866) to snap shut, and clamp into target tissue.

The invention having been disclosed in connection with the foregoing variations and examples, additional variations will now be apparent to persons skilled in the art. The invention is not intended to be limited to the variations specifically mentioned, and accordingly reference should be made to the appended claims rather than the foregoing discussion of preferred examples, to assess the scope of the invention in which exclusive rights are claimed.

I claim:

1. Endoscopic surgery clip-dispensing apparatus, comprising:
   an elongated dispensing sleeve extending rearwardly from a dispensing end, the sleeve defining:
     an elongated lumen;
     a left L-shaped opening on a left side of the sleeve having: a left enlarged closed end, a left open slot and a left opening into the left open slot from the left enlarged closed end; the left open slot extending from the left opening to a left front opening on the dispensing end of the sleeve;
     a right L-shaped opening on a right side of the sleeve, the right side of the sleeve being diametrically opposed to the left side of the sleeve, the right L-shaped opening having: a right enlarged closed end, a right open slot and a right opening into the right open slot from the right enlarged closed end; the right open slot extending from the right opening to a right front opening on the dispensing end of the sleeve;
     a left ramp constriction disposed in the lumen on the left side of the sleeve rearward of the left L-shaped opening and a right ramp constriction disposed in the lumen on the right side of the sleeve rearward of the right L-shaped opening;
     wherein the left and right enlarged closed ends are characterized by a major width and the left and right open slots are characterized by a minor width;
   an elongated clip having:
     a tail end;
     a left arm extending from the tail end having: a left rear half loop portion, a left crossover portion, and a first forward portion; wherein the left crossover portion is between the left rear half loop portion and the first forward portion; wherein the first forward portion comprises a first enlarged tab formation and a first jaw terminating in a first tip end;
     a right arm extending from the tail end having: a right rear half loop portion, a right crossover portion, and a second forward portion; wherein the right crossover portion is between the right rear half loop portion and the second forward portion; wherein the second forward portion comprises a second enlarged tab formation and a second jaw terminating in a second tip end;
   wherein the clip is configured to be loaded into the lumen such that the tail end is rearward of the left and right ramp constrictions;
   wherein the left and right rear half loop portions have a first width and the left and right crossover portions have a second width, the first second widths being less than the minor width; the first and second enlarged tab formations have a third width that is greater than the minor width and less than the major width;
   the tail end and the left and right ramp constrictions being configured such that the tail end can pass by the left and right ramp constrictions during use of the apparatus.

2. The endoscopic surgery clip-dispensing apparatus of claim 1, further comprising:
   a plurality of the clips loaded in the lumen in a series.

3. The endoscopic surgery clip-dispensing apparatus of claim 2, wherein:
   the plurality of clips includes a trailing most clip, and the apparatus further comprising a plunger for applying a forward pressure on the trailing most clip of the plurality of clips.

4. The endoscopic surgery clip-dispensing apparatus of claim 1, wherein:
   the left and right crossover portions overlap and are positioned in spaced parallel planes;
   the left and right crossover portions each have an outer surface that serves as a compressive cam surface when pushed past the left and right ramp constrictions respectively.

5. The endoscopic surgery clip-dispensing apparatus of claim 1, wherein:
   the apparatus is configured such that the second and first enlarged tab formations egress out of the lumen though the left and right enlarged closed ends respectively as a portion portion of each of the second and first jaws egress out of the lumen through the left and right open slots respectively.

6. The endoscopic surgery clip-dispensing apparatus of claim 1, wherein:
   the tail end is produced of a resilient material and serves as a spring-biased fulcrum providing jaw-clenching pressure to the clip.

7. The endoscopic surgery clip-dispensing apparatus of claim 1, wherein:
   the left enlarged closed end is defined in part by a left rear edge extending between and intersecting a pair of left side edges and a solid left shoulder extending from one of the pair of left side edges, the left shoulder being spaced from the left rear edge;
   the right enlarged closed end is defined in part by a right rear edge extending between and intersecting a pair of right side edges and a right shoulder extending from one of the pair of right side edges, the right shoulder being spaced apart from the right rear edge; and
   the first and second enlarged tab formations are wedge-shaped, the first enlarged tab formation including a first spreading cam surface, the second enlarged tab formation including a second spreading cam surface; the first and second spreading cam surfaces configured for engaging the right and left shoulders respectively to thereby open the first and second tip ends outside of the dispensing end of the sleeve.

8. The endoscopic surgery clip-dispensing apparatus of claim 7, wherein:
   the tail end is formed of a resilient material and serves as a spring-biased fulcrum providing jaw-clenching pressure to the clip;
   the sleeve further comprises a left pair of spreading bearing surfaces along a side of the left open slot and a right pair of spreading bearing surfaces along a side of the right open slot,
   the first enlarged tab formation comprises a first rear end and the second enlarged tab formation comprises a second rear end;
   the second and first enlarged tab formations are configured such that when pushed past the left and right shoulders respectively, the second enlarged tab formation rides on the left pair of spreading bearing surfaces and the first enlarged tab formation rides on the right pair of spreading bearing surfaces until the second and first rear ends clear the dispensing end to allow the second and first jaws to swing shut due to the spring-biased fulcrum of the tail end.

* * * * *